United States Patent [19]
Janzen et al.

[11] Patent Number: 5,405,967
[45] Date of Patent: Apr. 11, 1995

[54] SPIN-TRAP MOLECULES 2-TRIFLUOROMETHYL- OF 5,5-DIMETHYL-1-DYRROLINE-N-OXIDE

[75] Inventors: Edward G. Janzen; Yong-Kang Zhang, both of Oklahoma City, Okla.

[73] Assignee: Oklahoma Medical Research Foundation, Oklahoma City, Okla.

[21] Appl. No.: 142,589

[22] Filed: Oct. 22, 1993

[51] Int. Cl.⁶ .......................................... C07D 207/46
[52] U.S. Cl. ..................................................... 548/542
[58] Field of Search ......................................... 548/452

[56] References Cited

PUBLICATIONS

Tordeux, et al., "Synthese de la trifluoromethyl-vinyl-cetone," *J Fluorine Chemistry* 20:301–306 (1982).

Dess, et al., "Readily accessible 12-I-5 oxidant for the conversion of primary and secondary alcohols to aldehydes and ketones," *J Org Chem* 48:4155–4156 (1983).

Linderman, et al., "Oxidation of fluoroalkyl-substituted carbinols by the Dess–Martin reagent," *J Org Chem* 54:661–668 (1989).

*Primary Examiner*—David B. Springer
*Attorney, Agent, or Firm*—Richards, Medlock & Andrews

[57] ABSTRACT

Novel spin traps comprising 2-trifluoromethyl-1-DMPO or derivatives thereof have now been found. An effective synthesis method for these spin traps is also disclosed.

3 Claims, 20 Drawing Sheets

SPIN-TRAP MOLECULES 2-TRIFLUOROMETHYL- OF 5,5-DIMETHYL-1-DYRROLINE-N-OXIDE

TECHNICAL FIELD

This invention relates to the field of spin-trap molecules useful for trapping free radicals in biological systems and methods for preparation thereof.

BACKGROUND OF THE INVENTION

Scientists are continually researching for effective free radical trapping compounds, known as "spin-traps," since free radicals are believed to be involved in disease initiation and mediation in animals. Ischemia and inflammation are two examples of biological events in which free radicals have been implicated. Spin traps are important for diagnostic and therapeutic purposes. Known spin-traps shown to be effective in animal models include α-phenyl N-tert-butyl nitrone (PBN), α-(4-pyridyl-1-oxide)-N-tert-butyl nitrone (POBN), 2-methyl-2-nitrosopropane (MNP), and 5,5 dimethyl-1-pyrroline N-oxide (DMPO).

Despite the discovery of several spin-trap molecules, the need remains for additional compounds which are of increased stability and which work more effectively to trap free radicals in biological systems. There has long been a desire for a stable spin-trap agent, resistant to dimerization, which is lipophilic in nature to increase mobility in and out of cell membranes and which does not have a toxic functionality. It has also been desired to obtain spin-trap agents which trap free radicals faster than known agents.

Another problem in the art has been that proposed structures of desired spin-traps, which theoretically may provide some of the desired properties, are postulated from time to time, but synthesis has been difficult or impossible by known methods. It therefore has been desired that a convenient method of synthesis be available for a spin-trap agent having some or all of the above-described properties.

A further problem in the art has been that, normally, spin trap adducts (formed when the spin trap agent traps a free radical) cannot be directly studied by NMR methods. Adducts must be first reduced as with hydrazine and the hydroxylamine reduction product analyzed. The inability to directly detect spin trap adducts has hampered biological research into the effectiveness of spin-traps as drugs for trapping free-radicals and monitoring therapy.

SUMMARY OF THE INVENTION

A new spin-trap molecule, 5,5-dimethyl-2-trifluoromethyl-1-pyrroline N-oxide ("2-trifluoromethyl DMPO" or "2-CF$_3$-DMPO") has now been synthesized and characterized. This new molecule has advantages for use in trapping free radicals in biological systems since it is stable, possesses an inert, non-toxic and lipophilic trifluoromethyl functionality, and the trifluoromethyl function is a Nuclear Magnetic Resonance (NMR) marker useful for monitoring the spin-trap. The new 2-CF$_3$-DMPO molecule is expected to have greater mobility in and out of membranes, and has been determined to have a faster rate constant for trapping superoxide radical anions.

Derivatives of 2-CF$_3$-DMPO are also part of this invention which are expected to exhibit similar utility.

The invention also concerns use of the novel spin trap agents for treatment and diagnostic purposes.

The novel molecule, which could not be successfully synthesized by any known method, has been synthesized by a novel "one-pot" method which provides an effective and convenient procedure to obtain 2-CF$_3$-DMPO.

DETAILED DESCRIPTION OF THE INVENTION

Figure 1:
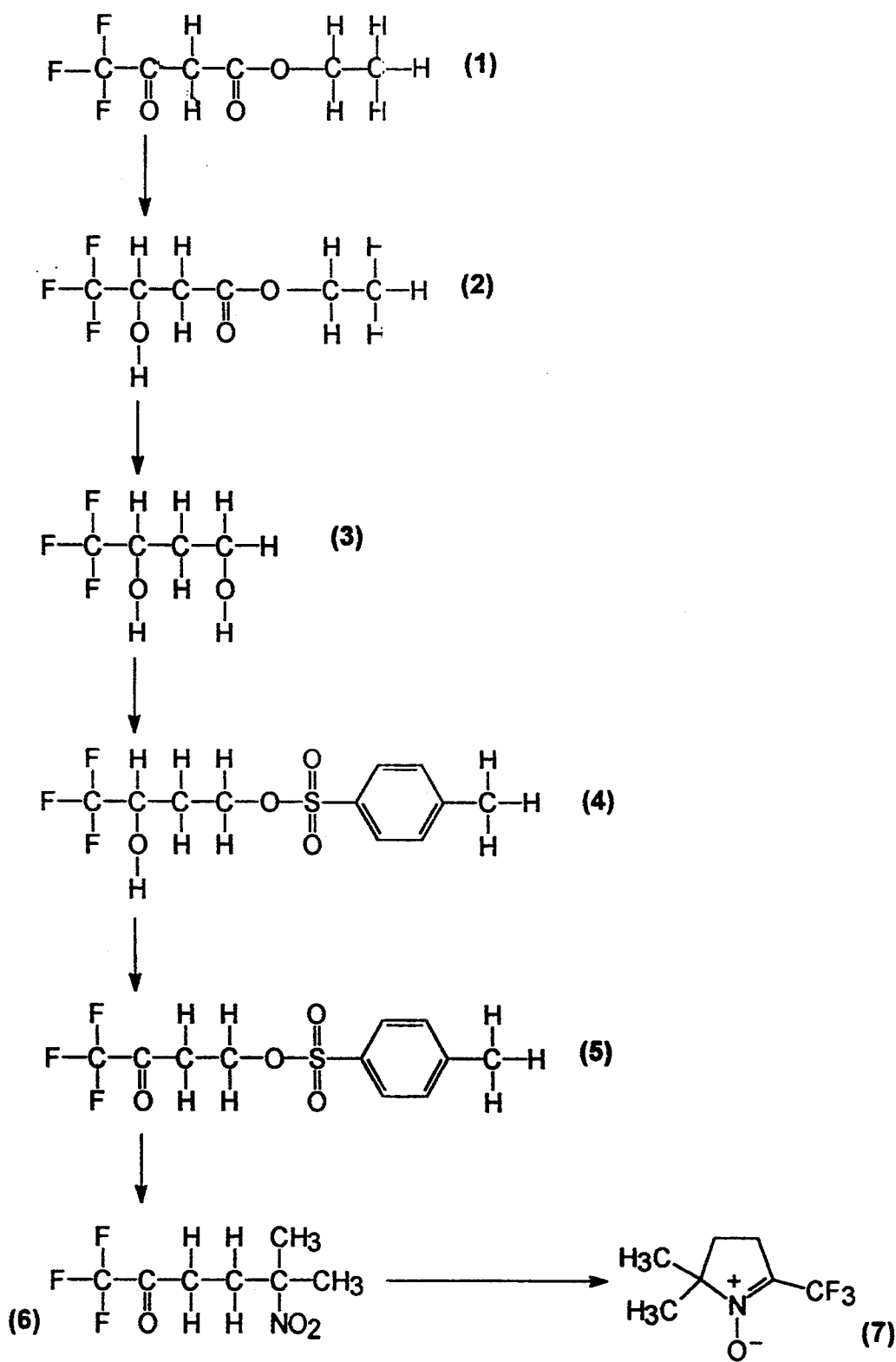
FIG. 1 depicts the preferred synthesis method for 2-CF$_3$-DMPO.

A new spin trap which includes a CF$_3$ moiety has been successfully synthesized. The new compound is 2-CF$_3$-DMPO and its derivatives. This spin trap is expected to exhibit several advantages as a biological spin trap agent. The new spin trap has the following structure:

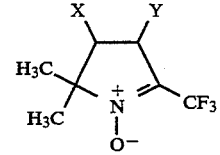

where X is H; alkyl (CH$_2$)$_n$H where n=(1, 2 ... 18); aryl; (CH$_2$)$_n$ COOR where n=(0, 1, 2 ... 18) and R=H, CH₃, CH₃—CH₂, or Group IA metal ions; (CH₂)$_n$ P(O) (OR)₂ where n=(0, 1, 2, ... 18), R=H, CH₃, CH₃—CH₂, or Group IA metal ions.

and Y is H; alkyl (CH₂)$_n$H where n=(1, 2 ... 18); aryl; (CH₂)$_n$ COOR where n=(0, 1, 2 ... 18) and R=H, CH₃, CH₃—CH₂, or Group IA metal ions; (CH₂)$_n$ P(O) (OR)₂ where n=(0, 1, 2, ... 18), R=H, CH₃, CH₃—CH₂, or Group IA metal ions.

X can be the same or different from Y in a given molecule.

One advantage is that the CF₃ can be used as a marker for NMR. The CF₃ function on the spin-trap agent herein disclosed makes it possible to use fluorine-NMR techniques to detect spin trap/spin adduct combinations. This detectable property is highly useful when it is desired to detect reduced spin-trap adducts in biological fluids.

When employed in in vitro tests, the CF₃ spin trap agent could be used to predict effectiveness in vivo and can be more easily monitored than reduced spin trap adducts not coming from trifluoromethyl substituted spin traps when NMR techniques are used.

The novel compound is believed to be superior to DMPO as a biological spin trap agent in that DMPO is too water soluble. 2-CF₃-DMPO is more lipophilic than DMPO, but the 2-CF₃ functionality is inert to undesirable reactions such as exhibited by other DMPO derivatives such as 2-methyl-DMPO.

Because of its lipophilic nature, 2-CF₃-DMPO can be used as a spin trap in membrane regions and trap free radicals which are formed in these areas.

Another related utility is believed to be site-specific defense against reactive free radicals created in the polar interface and in the outer aqueous layers of membranes. Prophylactic treatment of free-radical disorders is expected.

The utility of the compounds of the present invention in preventing or treating diseases is believed to be initiated or mediated by free-radical generation in the body. Exemplary doses range from 25 to 125 mg/kg of body weight in rats. The effective range of dosage in humans and other mammals is expected to be between about 25 to about 125 mg/kg, and preferably between about 25 to about 35 mg/kg of body weight. Particular dosage may vary depending on the particular derivative selected.

The compounds of the present invention are preferably administered systemically. The compounds can be administered at once, or can be divided into a number of smaller doses to be administered at varying intervals of times. The compounds may be administered orally or by other methods including intravenous, subcutaneous, topically and by intraperitoneal administration.

A method of administration of the compounds of the present invention is oral delivery. The compounds may be enclosed in capsules, compressed into tablets, microencapsulated, entrapped in liposomes, in solution or suspension, alone or in combination with a substrate immobilizing material such as starch or poorly absorbable salts. Pharmaceutically compatible binding agents and/or adjuvant materials can be used as part of a composition. Tablets or capsules can contain any of the following ingredients, or compounds of similar nature: a binder such as microcrystalline cellulose, gum tragacanth or gelatin; an excipient such as starch or lactose, an integrating agent such as alginic acid, or corn starch; a lubricant such as magnesium stearate; a glidant such as colloidal silicon dioxide; and sweetening and flavoring agents. When a capsule form is used the liquid carrier such as a fatty oil may be used. Capsules and tablets can be coated with sugar, shellac and other enteric agents as is known.

In another embodiment, the novel spin traps are useful as diagnostic agents to detect the site of free radical reactions, and probable tissue damage therefrom, in the body. The spin-traps can be radioactively labeled, or the CF₃-functionality could be employed as an NMR tag. In this embodiment, the spin trap agent would be administered to the animal and samples removed from blood and urine for testing.

The synthetic route for 2-CF₃-DMPO is illustrated in FIG. 1. Numerals in parenthesis in the discussion below refer to compounds so numbered in FIG. 1.

2,4-Dihydroxy-1,1,1-trifluorobutane (3) is prepared by sequential reduction of ethyl 4,4,4-trifluoroacetoacetate then ethyl 3-hydroxyl-4,4,4-trifluorobutyrate. Any effective reducing agent can be used. Most preferably, the reactions are conducted as follows. To a solution of ethyl 4,4,4-trifluoroacetoacetate (1) (18.4 g, 100 mmol) in ether (200 mL) is added sodium borohydride (NaBH₄) (4 g, 105 mmol) in several portions over a period of 30 min at 0°–5° C. The reaction mixture is stirred at 0°–5° C. for 1 hour and at room temperature overnight. Hydrochloric acid (10%, 100 mL) is carefully added and the solid is removed by filtration. The aqueous layer is extracted with ether (150 mL) and the combination is dried over Na₂SO₄, filtered and evaporated to give 18.0 g clear liquid (98%). The liquid comprises ethyl 3-hydroxy-4,4,4-trifluorobutyrate (2) (M. Tordeux and C. Wakselman, *J. Fluorine Chem.*, 20:301–306 (1982). The solution of the liquid in ether (50 mL) is added to a suspension of lithium aluminum hydride (6 g, 0.157 mol) in ether (50 mL) at 0°–5° C. for 80 minutes. After being stirred overnight at room temperature, 100 mL of 10% HCl is very carefully added to decompose excessive lithium aluminum hydride (LiAlH₄). The aqueous residue is extracted by ether or ethyl acetate (2×150 mL) and the combination dried, filtered and evaporated to afford 12.6 g clear liquid of 2,4-dihydroxy-1,1,1-trifluorobutane (FIG. 1, (3)). The above procedure was conducted and a yield of 88% obtained. The boiling point of compound (3) was 51.5°–54.0° C./0.32 mmHg. The structure was verified with ¹H Nuclear Magnetic Resonance (¹HNMR) as follows: (CDCl₃/TMS): δ8 6.05 (d, J=6.6 Hz, 1H, 2-OH), 4.60 (s, 1H, 4-OH), 4.03 (m, 1H, CH), 3.56 (s, 2H, 4—CH₂), 1.59 (m, 2H, 3-CH₂) ppm. This compound was previously described by M. Tordeux, et al., *J. Fluorine Chem.* 20:301–306 (1982).

Compound (3) is then selectively monotosylated on the terminal hydroxy group to give the desired 2-hydroxy-4-tosyloxy-1,1,1-trifluorobutane CF₃—CH(OH)—CH₂—CH₂—OSO₂—C₆H₄—CH₃ ((4) in FIG. 1). Most preferably, 2-hydroxy-4-tosyloxy-1,1,1-trifluorobutane (4) is prepared as follows. To a solution of compound (3) (12.6 g, 87.5 mmol) and pyridine (30 mL) in dichloromethane, 4-toluenesulfonyl chloride ("TsOCl") (20.5 g, 108 mmol) is added within 30 min. The solution is stirred for 4 days at 4° C. and then poured into a mixture of 10% HCl (100 mL) and ice. The organic layer is washed successively with 10% HCl (100 mL) and NaCl-saturated dilute Na₂CO₃ aqueous solution (100 mL). The solution is dried, filtered and evaporated to give a mixture which when chromatographed on silica gel elutes with CH₂Cl₂ ($R_f$=0.22) affording 14.25 g of clear liquid (4). The above procedure was conducted and a 55% yield obtained. The structure of (4) was confirmed by Mass Spectrometry (MS) and ¹HNMR, as the following results indicate. MS (rel. int. %): m/z=298 (M+, 49), 297 (M+-1, 21), 278 (M+-*HF*, 23), 277 (9), 229 (M+-CF₃, 2), 173 (100), 172 (32), 155 (12), 106 (24), 93 (13); ¹HNMR (CDCl₃/TMS): 7.80 (d, J=8.4 Hz, 2H, H—Ar), 7.38 (d, J=8.4 Hz, 2H, H—Ar), 4.30 (dt, J₁=3.9 Hz, J₂=10.2 Hz, 1H, CHCF₃), 4.15 (m, 2H, 4-CH₂), 3.20 (d, J=5.7 Hz, 1H, OH), 2.44 (s, 3H, CH₃), 2.06 and 1.84 (m, 2H, 3-CH₂) ppm.

The oxidation of the CF₃CH(OH)— moiety of compound (4) is then accomplished. Most preferably, a specific periodinane oxidant, shown as compound (9) below, (also known as "Dess-Martin reagent") is employed. The oxidant (9) is generally prepared from 2-iodobenzoic acid by oxidation with potassium bromate to give compound (8) which is reacted with acetic anhydride ("Ac₂O") and acetic acid ("AcOH") at 100° C. (D. B. Dess and J. C. Martin, *J. Org. Chem.*, 48:4155–56 (1983)). Periodinane (9) more specifically, is prepared as follows: To a three-necked 5-liter flask, 2-iodobenzoic acid (85.2 g, 0.34 mol) and 0.73M H₂SO₄ (730 mL) is added. With mechanical stirring, KBrO₃ (76.0 g, 0.45 mol) is added over a period of 45 min keeping the temperature below 55° C. Bromine is generated from the oxidation reaction. The mixture is vigorously stirred for additional 4 hours at ca. 65° C. After being cooled to 0°–5° C., filtration is followed by washing the solid with water (1000 mL) and ethanol (2×50 mL). The resulted solid is dried by pumping in the presence of drying agent. The above procedure was conducted and the cyclic product (8) (89.0 g, 93% yield) was obtained. Part of (8) (50 g, 0.179 mol) is then mixed with acetic anhydride (160 mL, 1.70 mol) and acetic acid (140 mL) in a N₂ atmosphere. The mixture is heated to 100° C. and stirred for an additional 30 min after the solid was dissolved. The solution is cooled to room temperature and the liquid is removed by vacuum (0.5 mmHg). Filtration is conducted in the atmosphere of nitrogen and the solid washed with ether (300 mL). The solid is pumped to completely remove the presented liquid. When the above was conducted, 64.7 g (yield 85%) of the periodinane oxidant (9) was obtained.

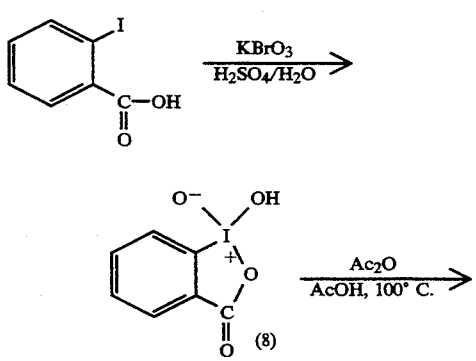

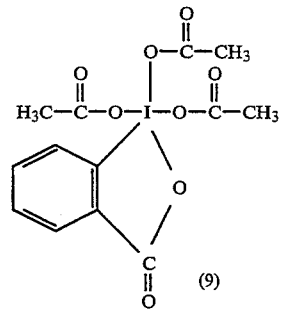 (9)

The monotosylate (4) is preferably oxidized (R. J. Linderman and D. M. Graves, *J. Org. Chem.*, 54:661–668 (1989)) with 3.7 equivalents of oxidant (9) to generate the corresponding ketone 4-tosyloxy-1,1,1-trifluoro-2-butanone (5):

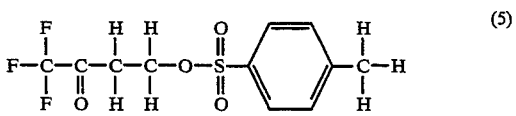 (5)

Preferably, 4-tosyloxy-1,1,1-trifluoro-2-butanone (5) is prepared as follows: A dry N₂ flow is allowed to pass through a bottle containing an oxidant (9) (10.0 g, 23.6 mmol) to remove possibly-presented acetic anhydride. In a while, dichloromethane (100 mL) is added to dissolve the solid. A solution of (4) (1.9 g, 6.3 mmol) in dichloromethane (40 mL) is added and the bottle sealed with a stopper. After being stirred at room temperature for 4.5 h, the mixture is poured into aqueous sodium bisulfite solution with stirring. A Na₂CO₃-saturated aqueous solution (100 mL) is slowly added and the aqueous layer is extracted with dichloromethane (2×50 mL). The organic combination is washed with water (100 mL), dried over MgSO₄, filtered and evaporated to give about 1.9 g of clear liquid (5) comprising 4-tosyloxy-1,1,1-trifluoro-2-butanone. The procedure above was conducted and the structure of the product was confirmed with ¹HNMR: (CDCl₃/TMS): 7.76 (d, J=8.4 Hz, 2H, H—Ar), 7.36 (d, J=8.7 Hz, 2H, H—Ar), 4.32 (t, J=5.9 Hz, 2H, 4-CH₂), 3.11 (t, J=5.7 Hz, 2H, 3-CH₂), 2.45 (s, 3H, CH₃) ppm. The yield was 100% (range 74–100%). The tosylated ketone (5) is treated with 10-fold (CH₃)₂C(Na)NO₂ in ethanol at 0°–5° C. and solid is immediately generated from the homogeneous solution. An elimination addition reaction results in the desired nitroketone compound 5-methyl-5-nitro-1,1,1-trifluoro-2-hexanone (6).

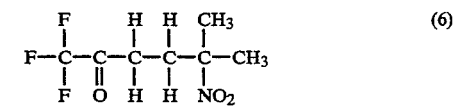 (6)

Most preferably, 5-methyl-5-nitro-1,1,1-trifluoro-2-hexanone (6) is prepared as follows: A mixture of 2-nitropropane (17.5 g, 196.5 mmol) and 21% wt. sodium ethoxide (42.4 g, 131 mmol) in ethanol (150 mL) is cooled to 0°–5° C. with an ice-water bath in a nitrogen atmosphere. Ketone (5) (3.9 g, 13.1 mmol) in 50 mL of ethanol is added. In about 2 min, solid is generated from the homogeneous solution. The mixture is stirred for two hours at 0°–5° C., then for 6 hours at room temperature. Concentrated hydrochloric acid (15 mL) is slowly added with cooling. The solid is removed by filtration and the solution evaporated. The residue is dissolved in chloroform (150 mL), washed with NaCl—saturated water (2×100 mL). The organic layer is dried over MgSO$_4$, filtered and evaporated. When conducted, this method gave 2.7 g brown liquid (96% range 94–100%) which was distilled to afford 2.1 g (75% yield) of colorless liquid (6); b.p. 46° C./0.18 mmHg. $^1$HNMR (CDCl$_3$/TMS): δ6 2.77 (t, J=7.4 Hz, 2H, 3-CH$_2$),2.28 (t, J=7.6 Hz, 2H, 4-CH$_2$),1.61 (s, 6H, 2 CH$_3$) ppm.

The nitro-ketone (6) is then reduced. Most preferably, it is reduced with zinc and acetic acid in 95% EtOH at 0°–5° C. to afford the nitrone spin trap 5,5-dimethyl-2-trifluoromethyl-1-pyrroline N-oxide (7). More specifically, 5,5-dimethyl-2-trifluoromethyl-1-pyrroline N-oxide (7) is prepared as follows: Zinc dust (1.26 g, 19.2 mmol) is added to a solution of (6) (2.05 g, 9.6 mmol) in 95% ethanol (60 mL) which has been cooled to 3° C. with ice-water bath. With a vigorously mechanical stirring, acetic acid (2.31 g, 38.5 mmol) in 95% ethanol (20 mL) is added dropwise for 10 min at <7° C. The reaction mixture is stirred for additional 3 h at 3° C., then filtered. The solid is washed with 95% EtOH (50 mL). The residue after evaporation is dissolved in chloroform (150 mL) and the solution washed with NaCl-saturated water (2×50 mL). The chloroform solution is dried over MgSO$_4$, filtered and evaporated. When conducted, 1.22 g (70% yield) of clear liquid of which the relative distance traveled by a spot and by the solvent front (R$_f$) of the single spot is 0.22 (CH$_2$Cl$_2$) was obtained. Distillation afforded 1.1 g (63%) of colorless liquid; b.p. 44° C./0.18 mmHg. MS (rel. int. %): m/z=181 (M+,84) 166 (M+-CH$_3$, 25), 162 (20), 152 (8) 149 (37), 69 (CF$_3$+, 100); $^1$HNMR (CDCl$_3$/TMS): δ2.78 (tm, J$_t$=7.4 Hz, 2H, 3-CH$_2$), 2.13 (t, J=7.4 Hz, 2H, 4-CH$_2$), 1.402 (s, 3H, CH$_3$), 1.398 (s, 2H, CH$_3$) ppm.

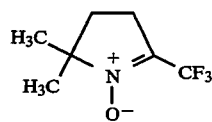

(7)

Derivatives of 2-CF$_3$-DMPO could be made by the following preferred synthesis method:

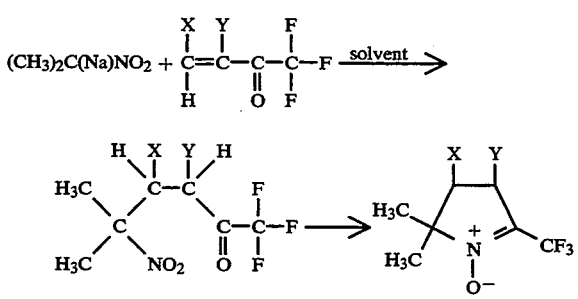

The structure of such derivatives is:

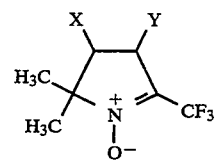

where X is alkyl (CH$_2$)$_n$H where n=(1, 2 . . . 18); aryl; (CH$_2$)$_n$ COOR where n=(0, 1, 2 . . . 18) and R=H, CH$_3$, CH$_3$—CH$_2$, or Group IA metal ions; (CH$_2$)$_n$ P(O) (OR)$_2$ where n=(0, 1, 2, . . . 18), R=H, CH$_3$, CH$_3$—CH$_2$, or Group IA metal ions. and Y is alkyl (CH$_2$)$_n$H where n=(1, 2 . . . 18); aryl; (CH$_2$)$_n$ COOR where n=(0, 1, 2 . . . 18) and R=H, CH$_3$, CH$_3$—CH$_2$, or Group IA metals; (CH$_2$)$_n$ P(O) (OR)$_2$ where n=(0, 1, 2, . . . 18), R=H, CH$_3$, CH$_3$—CH$_2$, or Group IA metal ions.

X can be the same or different from Y in a given molecule.

EXAMPLE 1

Comparison of 2-CF$_3$-DMPO with DMPO: Trapping of O$_2^-$

Equal concentrations (0.025M) of 2-CF$_3$-DMPO and DMPO were dissolved in a same 30% H$_2$O$_2$ solution, and irradiated with ultraviolet (UV) radiation for 2 to 5 seconds. The sample was tested by determining their EPR signals by standard methods.

The EPR signals of 2-CF$_3$-DMPO-O$_2^-$-adduct were found to be dominant. DMPO-O$_2^-$ signals were not detected.

The result indicates that 2-CF$_3$-DMPO traps O$_2^-$ radicals more rapidly than DMPO.

EXAMPLE 2

Comparison of 2-trifluoromethyl-DMPO with DMPO: Trapping of OH

2-CF$_3$-DMPO and DMPO were dissolved in a same 1% H$_2$O$_2$ solution. The solution was irradiated with UV as in Example 1. Table 1 shows the data, which indicates that while the OH trapping rate is not significantly different for the two spin-trap agents, the 2-CF$_3$-DMPO-OH adduct is more persistent than DMPO-OH.

TABLE 1

| EPR Spectrum | Time (min.) | | | | |
|---|---|---|---|---|---|
| Peak Height | 0 | 5 | 9.8 | 19.5 | 35 |
| DMPO—OH | 3.17 | 2.39 | 1.85 | 1.15 | 0.57 |
| 2-CF$_3$—DMPO—OH | 3.91 | 3.62 | 3.46 | 3.2 | 2.96 |

The t$_{\frac{1}{2}}$ for DMPO-OH was 15 minutes, while the t$_{\frac{1}{2}}$ for 2-CF$_3$-DMPO-OH was 72 minutes.

EXAMPLE 3

EPR Measurements for various 2-CF$_3$-DMPO adducts

Electron paramagnetic resonance spectroscopy (EPR) was used to measure the product of various trapping reactions conducted with 2-CF$_3$-DMPO as a spin-trapping agent. Data is shown in Table 3. EPR was conducted according to standard methods on the relatively stable radical compounds, or adducts, obtained from the reaction. The column entitled "Resource" indicates how the radical was produced. Where "Simulation" is indicated, a computer program was used to construct the EPR spectrum. The EPR spectrum determined the Hyperfine splitting constant $a_N$ ("HFSC"), fluorine atom HFSC $a_F$, and occasionally the hydrogen atom HFSC, $a_H$. The HFSC is measured in gauss or "G" which indicates the distance between peaks.

$t_{\frac{1}{2}}$ is a measure of stability of the adduct. The larger the $t_{\frac{1}{2}}$ value, the more stable the adduct, and the more useful the particular spin-agent in trapping the free radical concerned.

Selected EPR spectra data of 2-CF$_3$-DMPO adducts can be found in FIGS. 2–19.

TABLE 2A
EPR SETTINGS FOR FIGS. 2–5

Figure 2:
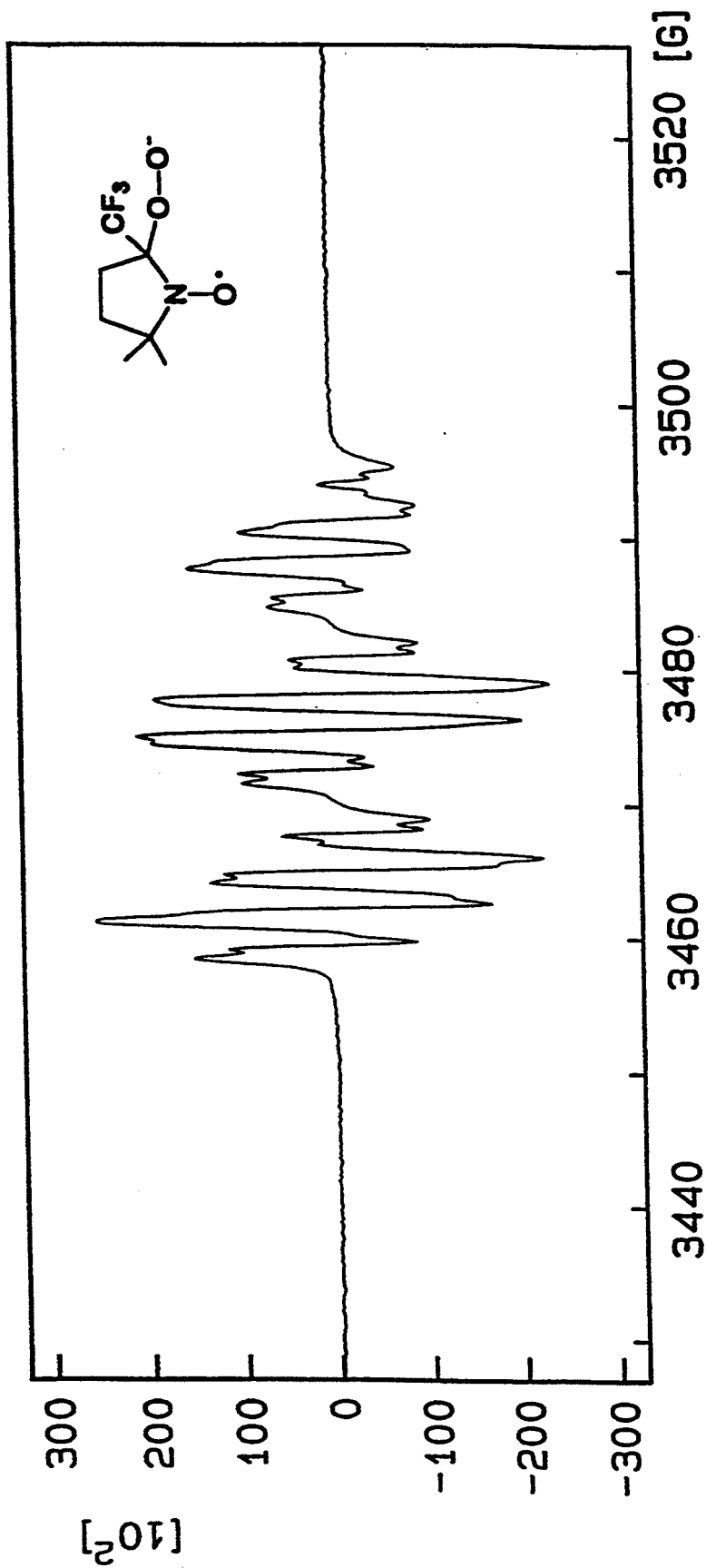
FIG. 2 is Electron Paramagnetic Resonance Spectroscopy (EPR) data on 2-CF$_3$-DMPO/O$_2-$ adduct.
Figure 3:
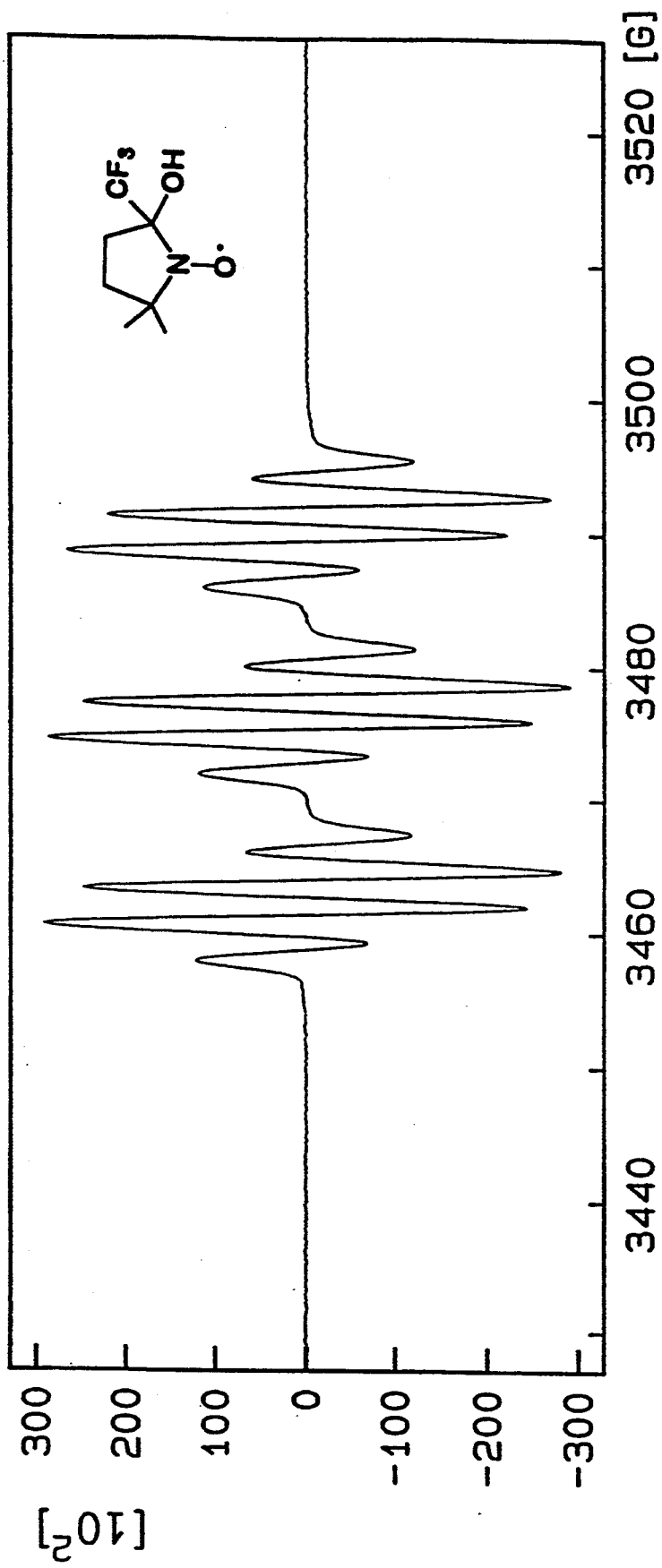
FIG. 3 is EPR data on 2-CF$_3$-DMPO/OH adduct.
Figure 4:
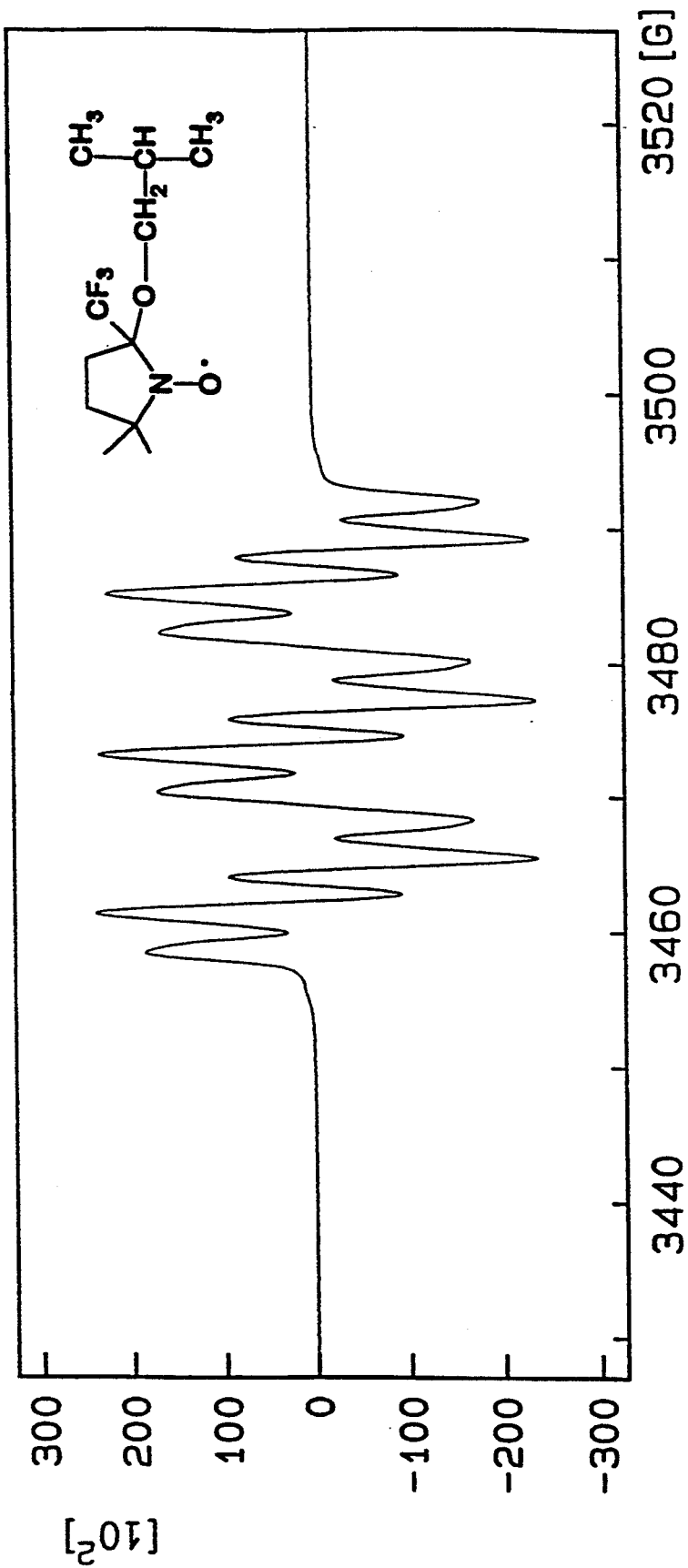
FIG. 4 is EPR data on 2-CF$_3$-DMPO/i-butyloxy adduct.
Figure 5:
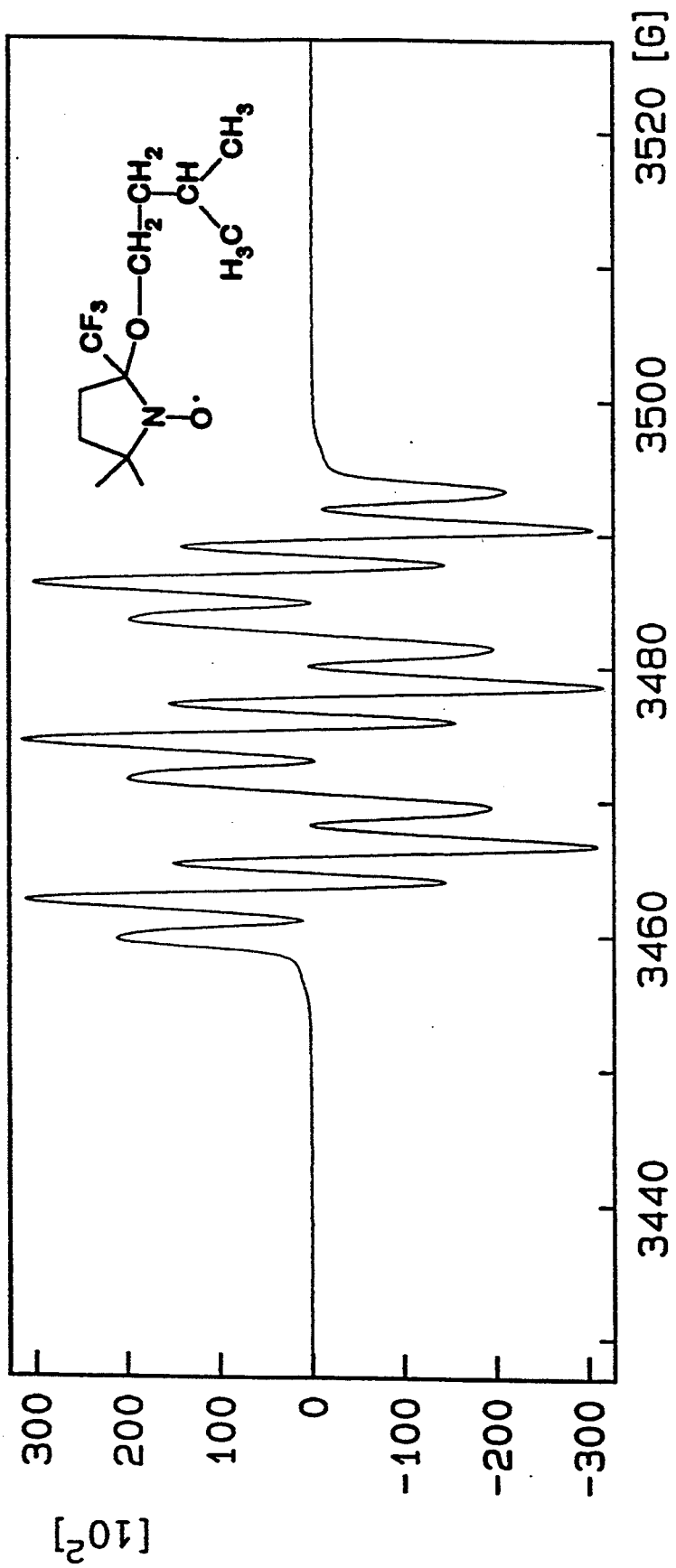
FIG. 5 is EPR data on 2-CF$_3$-DMPO/i-amyloxy adduct.

| | FIG. 2 | FIG. 3 | FIG. 4 | FIG. 5 |
|---|---|---|---|---|
| Receiver | | | | |
| Receiver Gain | 1.00e + 05 | 2.50e + 04 | 1.00e + 04 | 1.00e + 04 |
| Phase (deg) | 0 | 0 | 0 | 0 |
| Harmonic | 1 | 1 | 1 | 1 |
| Mod Freq (kHz) | 100.0000 | 100.0000 | 100.0000 | 100.0000 |
| Mod Amplitude (G) | 0.254 | 1.011 | 1.011 | 1.011 |
| Signal Channel | | | | |
| Conversion (ms) | 40.96 | 81.92 | 81.92 | 81.92 |
| Time Const (ms) | 81.92 | 40.96 | 40.96 | 40.96 |
| Sweep Time (s) | 41.943 | 83.886 | 83.886 | 83.886 |
| Scale | 16 | 16 | 16 | 16 |
| Field | | | | |
| Center Field (G) | 3477.00 | 3477.00 | 3477.00 | 3477.00 |
| Sweep Width (G) | 100.00 | 100.00 | 100.00 | 100.00 |
| Resolution (points) | 1024 | 1024 | 1024 | 1024 |
| Comment: | 2-CF$_3$ DMPO (1% v.) in 30% H$_2$O$_2$.UV3s | 2-CF$_3$—DMPO (.02M) & 1% H$_2$O$_2$.H$_2$O.UV 3s + 3s.CF$_3$ DMPO—OH Radical | CF$_3$DMPO (.02M) + 1 μL iso-BuONO C$_6$H$_6$.UV2s.2-CF$_3$—DMPO—OBu-iso. | CF$_3$DMPO (.02M) + 1 μL iso-Amyl—ONO C$_6$H$_6$.UV2s. iso-AmylO-2-CF$_3$DMPO. |

TABLE 2B
EPR SETTINGS FOR FIGS. 6–9

Figure 6:
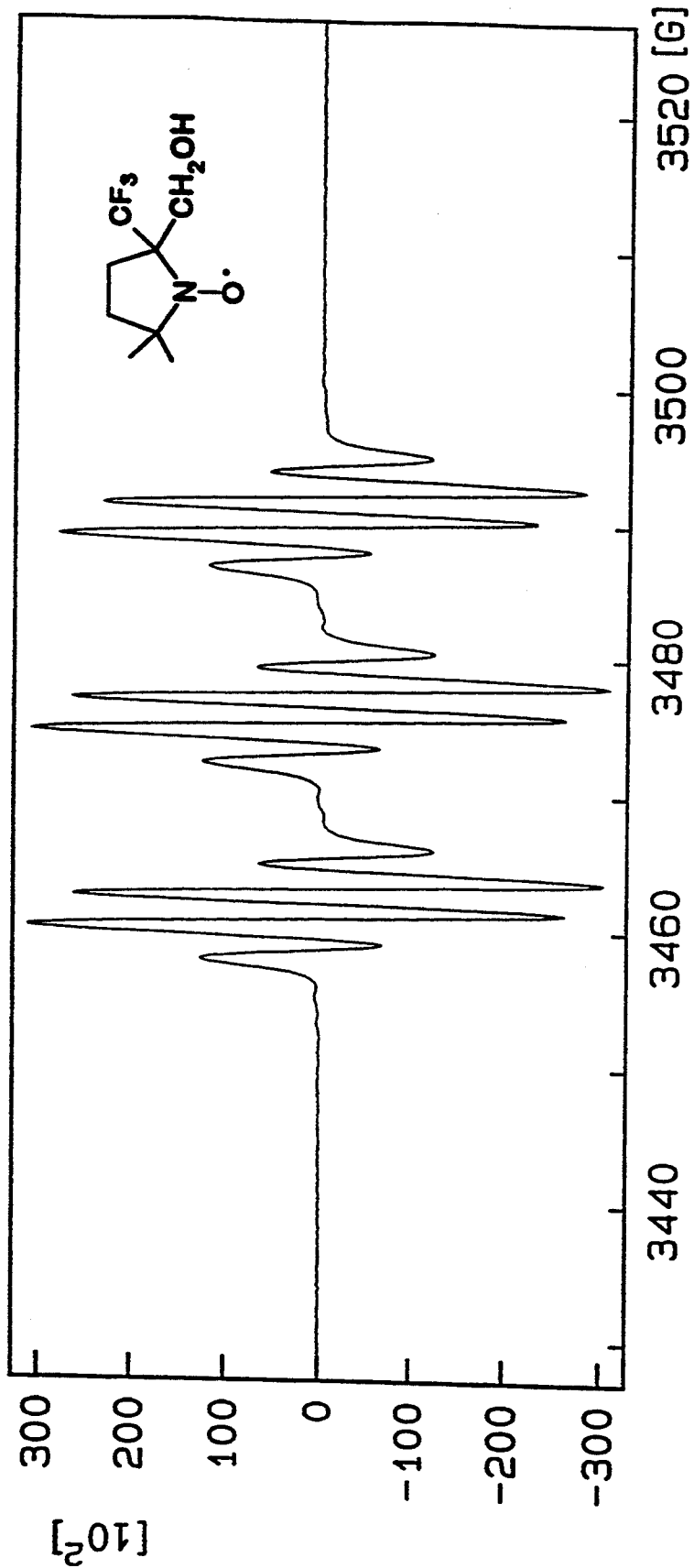
FIG. 6 is EPR data on 2-CF$_3$-DMPO/HOCH$_2$ adduct.
Figure 7:
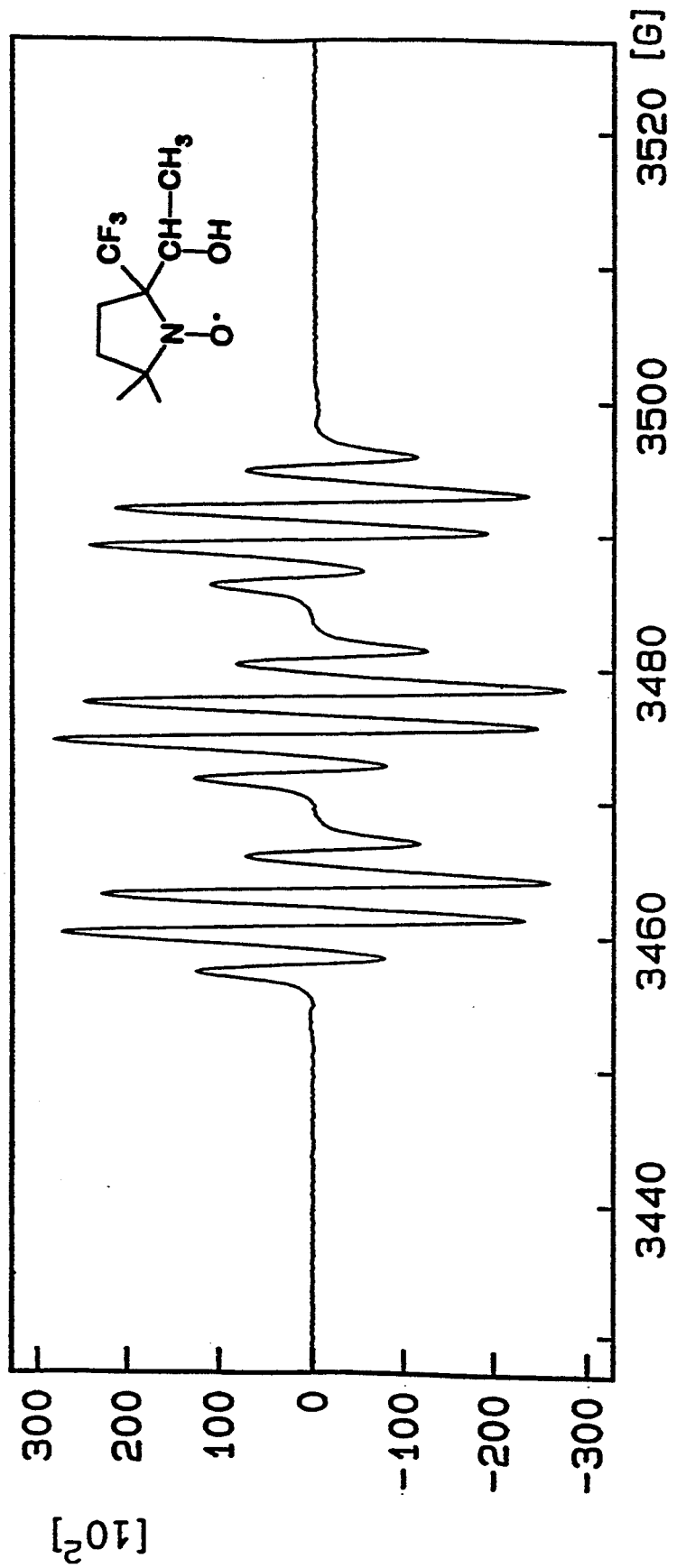
FIG. 7 is EPR data on 2-CF$_3$-DMPO/1-hydroxyethyl adduct.
Figure 8:
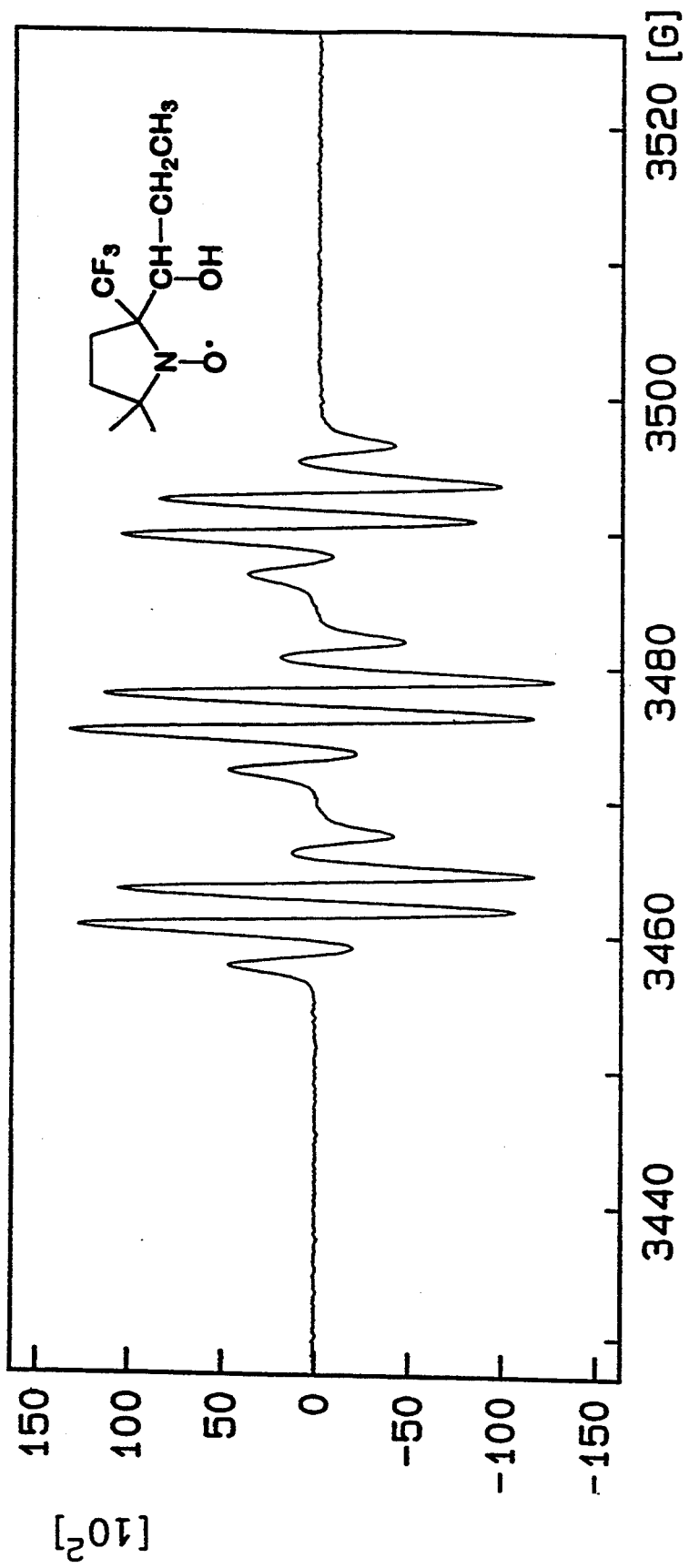
FIG. 8 is EPR data on 2-CF$_3$-DMPO/1-hydroxypropyl adduct.
Figure 9:
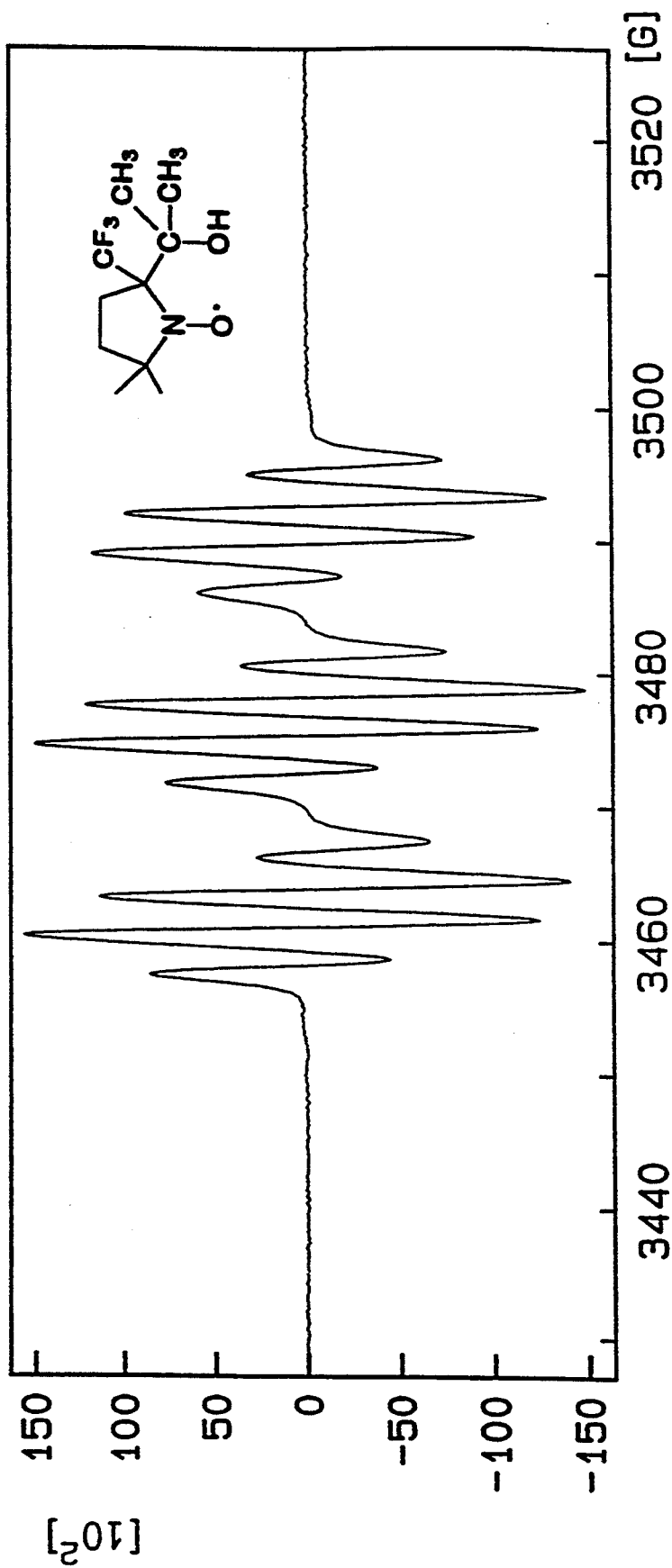
FIG. 9 is EPR data on 2-CF$_3$-DMPO/(CH$_3$)$_2$ COH adduct.

| | FIG. 6 | FIG. 7 | FIG. 8 | FIG. 9 |
|---|---|---|---|---|
| Receiver | | | | |
| Receiver Gain | 1.60e + 04 | 2.50e + 04 | 2.00e + 04 | 2.00e + 04 |
| Phase (deg) | 0 | 0 | 0 | 0 |
| Harmonic | 1 | 1 | 1 | 1 |
| Mod Freq (kHz) | 100.0000 | 100.0000 | 100.0000 | 100.0000 |
| Mod Amplitude (G) | 1.011 | 1.011 | 1.011 | 1.011 |
| Signal Channel | | | | |
| Conversion (ms) | 81.92 | 81.92 | 81.92 | 81.92 |
| Time Const (ms) | 40.96 | 40.96 | 40.96 | 40.96 |
| Sweep Time (s) | 83.886 | 83.886 | 83.886 | 83.886 |
| Scale | 16 | 16 | 15 | 15 |
| Field | | | | |
| Center Field (G) | 3477.00 | 3477.00 | 3477.00 | 3477.00 |
| Sweep Width (G) | 100.00 | 100.00 | 100.00 | 100.00 |
| Resolution (points) | 1024 | 1024 | 1024 | 1024 |
| Comment: | 2-CF$_3$—DMPO (.02M) & 1% H$_2$O$_2$ & 10% v. MeOH.H$_2$O.UV5s. CF$_3$DMPO—CH$_2$OH | 2-CF$_3$—DMPO (.02M) & 1% H$_2$O$_2$ & 10% v. EtOH.H$_2$O.UV3s. 2-CF$_3$DMPO—CH(OH) Me. | 2-CF$_3$DMPO (.02M) & 1% H$_2$O$_2$ & 10% v. EtCH$_2$OH.H$_2$O. UV5s | 2-CF$_3$DMPO (.02M) & 1% H$_2$O$_2$ & 10% v. iso-EtCH$_2$OH. H$_2$O.UV5s + 10s + 10s + 10s |

TABLE 2C
EPR SETTINGS FOR FIGS. 10–13

Figure 10:
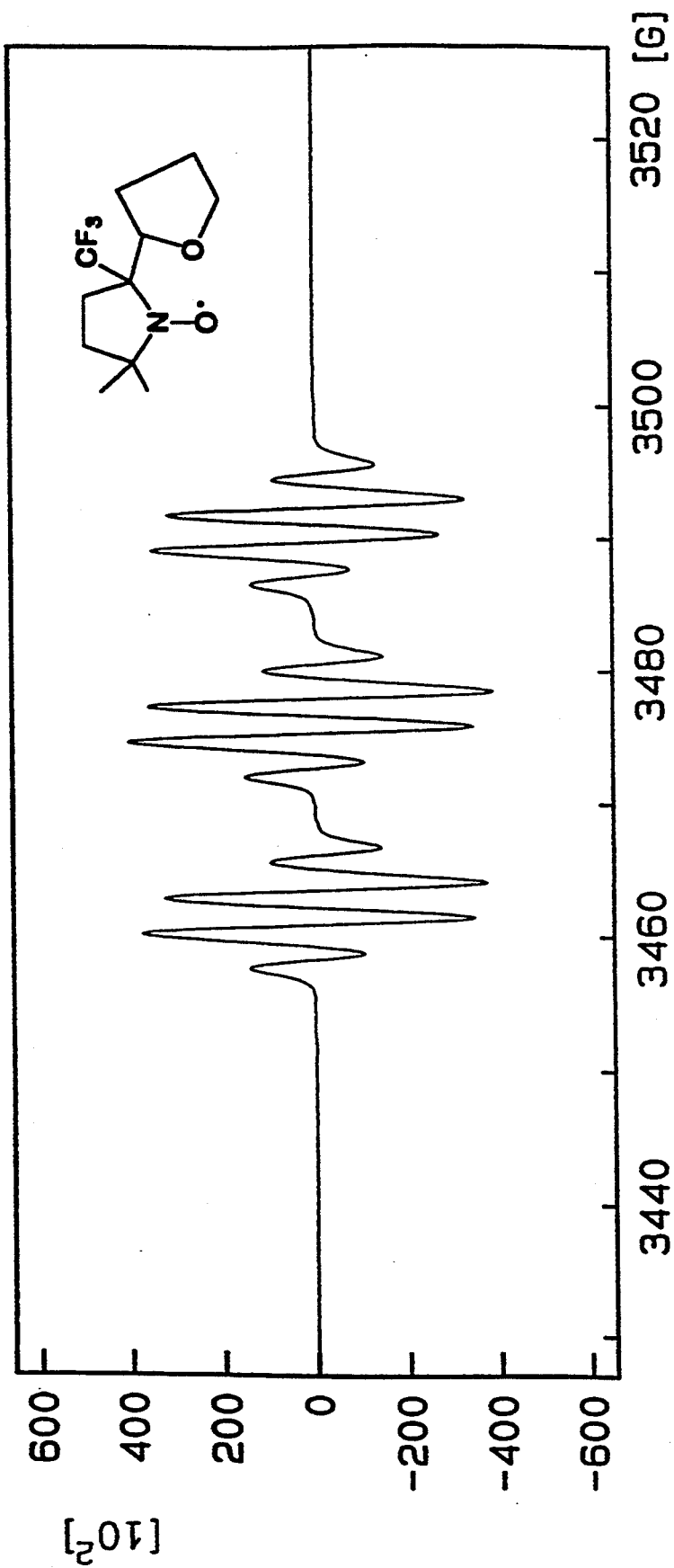
FIG. 10 is EPR data on 2-CF$_3$-DMPO/tetrahydrofuryl adduct.
Figure 11:
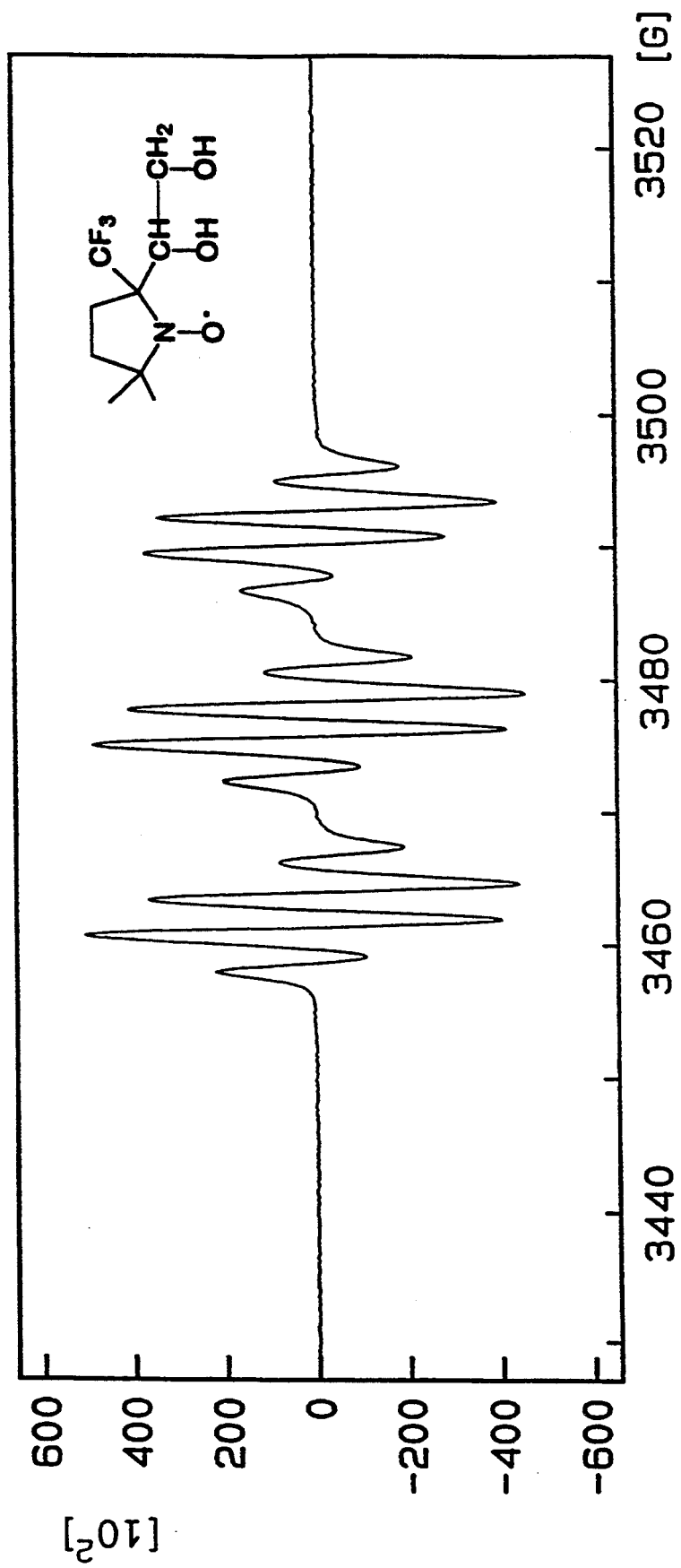
FIG. 11 is EPR data on 2-CF$_3$-DMPO/HOCH$_2$CH$_2$OH adduct.
Figure 12:
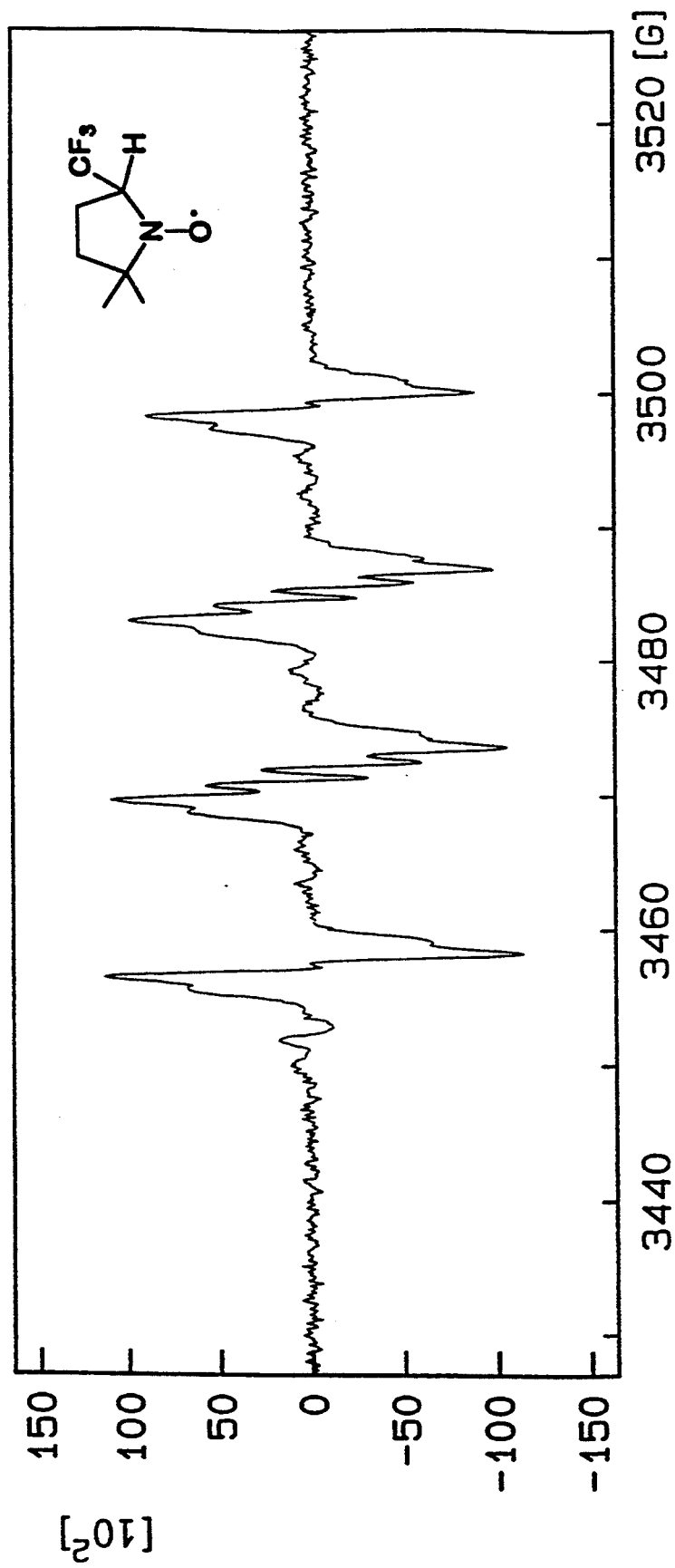
FIG. 12 is EPR data on 2-CF$_3$-DMPO/Bu$_3$ SnH adduct (Run 1)
Figure 13:
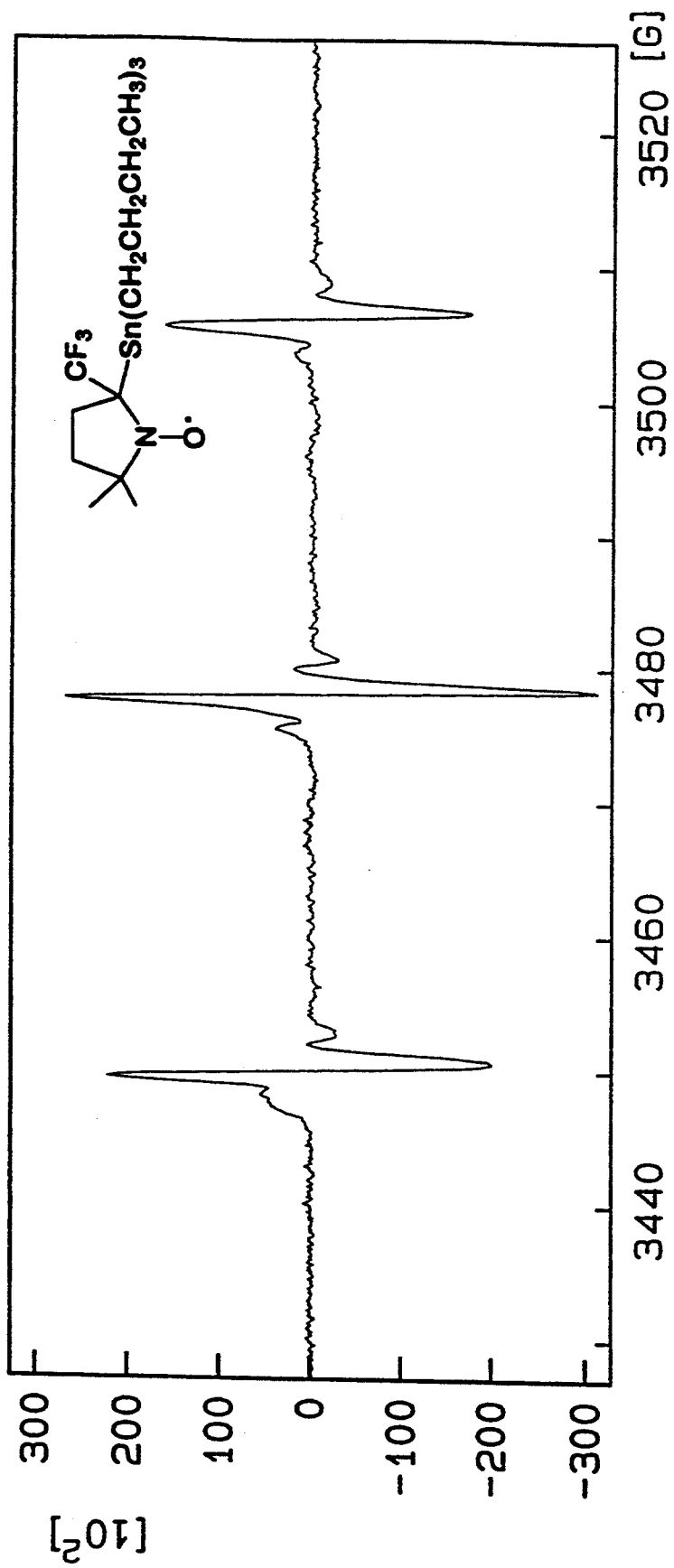
FIG. 13 is EPR data on 2-CF$_3$-DMPO/Bu$_3$ SnH adduct (Run 2).

| | FIG. 10 | FIG. 11 | FIG. 12 | FIG. 13 |
|---|---|---|---|---|
| Receiver | | | | |
| Receiver Gain | 1.00e + 04 | 5.00e + 04 | 1.00e + 05 | 1.00e + 05 |
| Phase (deg) | 0 | 0 | 0 | 0 |
| Harmonic | 1 | 1 | 1 | 1 |
| Mod Freq (kHz) | 100.0000 | 100.0000 | 100.0000 | 100.0000 |
| Mod Amplitude (G) | 1.011 | 1.011 | 0.320 | 0.113 |
| Signal Channel | | | | |
| Conversion (ms) | 81.92 | 81.92 | 81.92 | 81.92 |
| Time Const (ms) | 40.96 | 40.96 | 40.96 | 40.96 |
| Sweep Time (s) | 83.886 | 83.886 | 83.886 | 83.886 |
| Scale | 17 | 17 | 15 | 16 |
| Field | | | | |
| Center Field (G) | 3477.00 | 3477.00 | 3477.00 | 3477.00 |
| Sweep Width (G) | 100.00 | 100.00 | 100.00 | 100.00 |
| Resolution (points) | 1024 | 1024 | 1024 | 1024 |

TABLE 2C-continued

| | EPR SETTINGS FOR FIGS. 10–13 | | | |
|---|---|---|---|---|
| | FIG. 10 | FIG. 11 | FIG. 12 | FIG. 13 |
| Comment: | 2-CF$_3$DMPO (.02M) & 1% H$_2$O$_2$ & 10% v. THF.H$_2$O.UV5s + 20s.CF$_3$—DMPO —THF Radical | 2-CF$_3$DMPO (.02M) & 1% H$_2$O$_2$ & 10% v. HOCH$_2$CH$_2$OH. H$_2$O.UV5s + 23s + 20s | 2-CF$_3$DMPO (.02M) & 2.5% v.Bu$_3$SnH C$_6$H$_6$.UV5s + 5s | 2-CF$_3$DMPO (.02M) & 7.5% v.Bu$_3$SnH C$_6$H$_6$.UV10s again |

TABLE 2D

Figure 14:
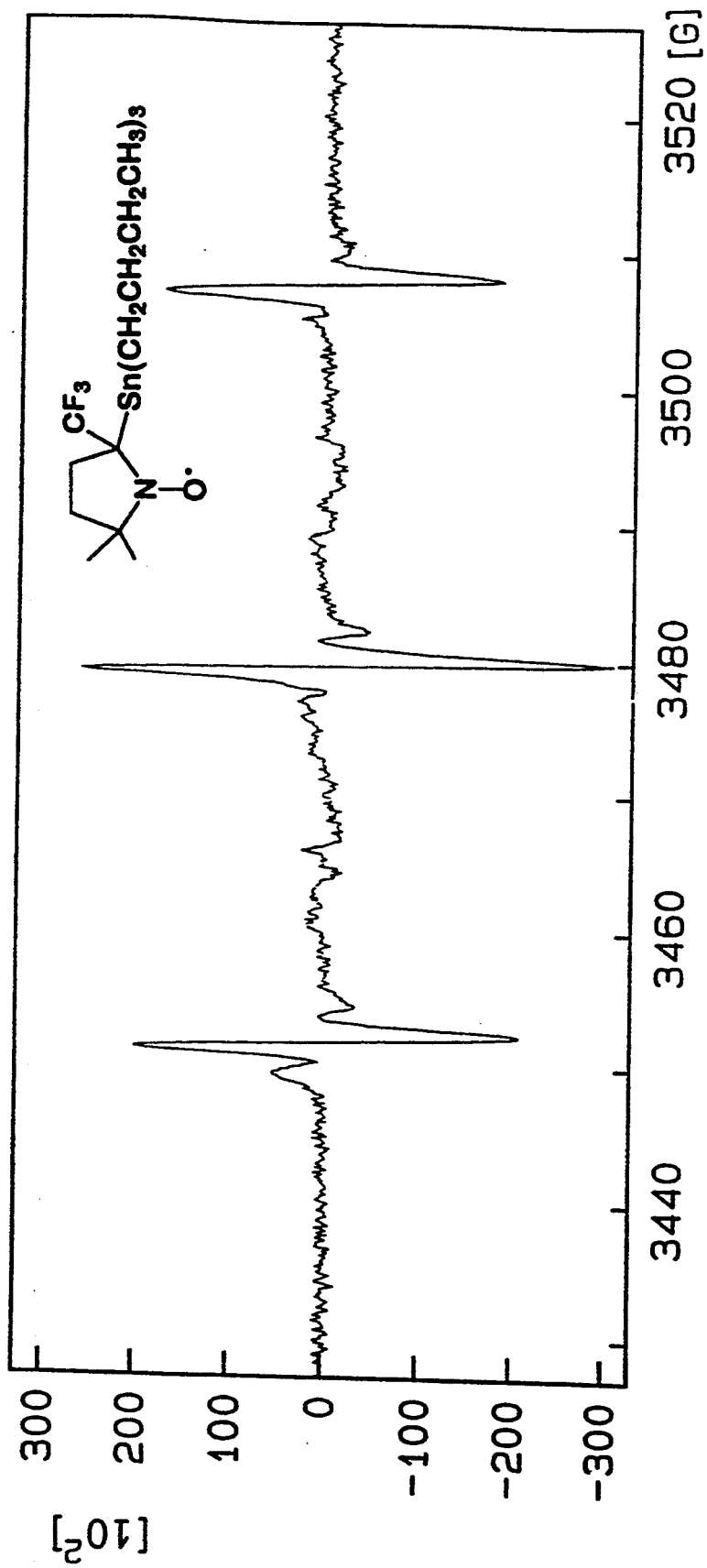
FIG. 14 is EPR data on 2-CF$_3$-DMPO/Bu$_3$ SnD adduct.
Figure 15:
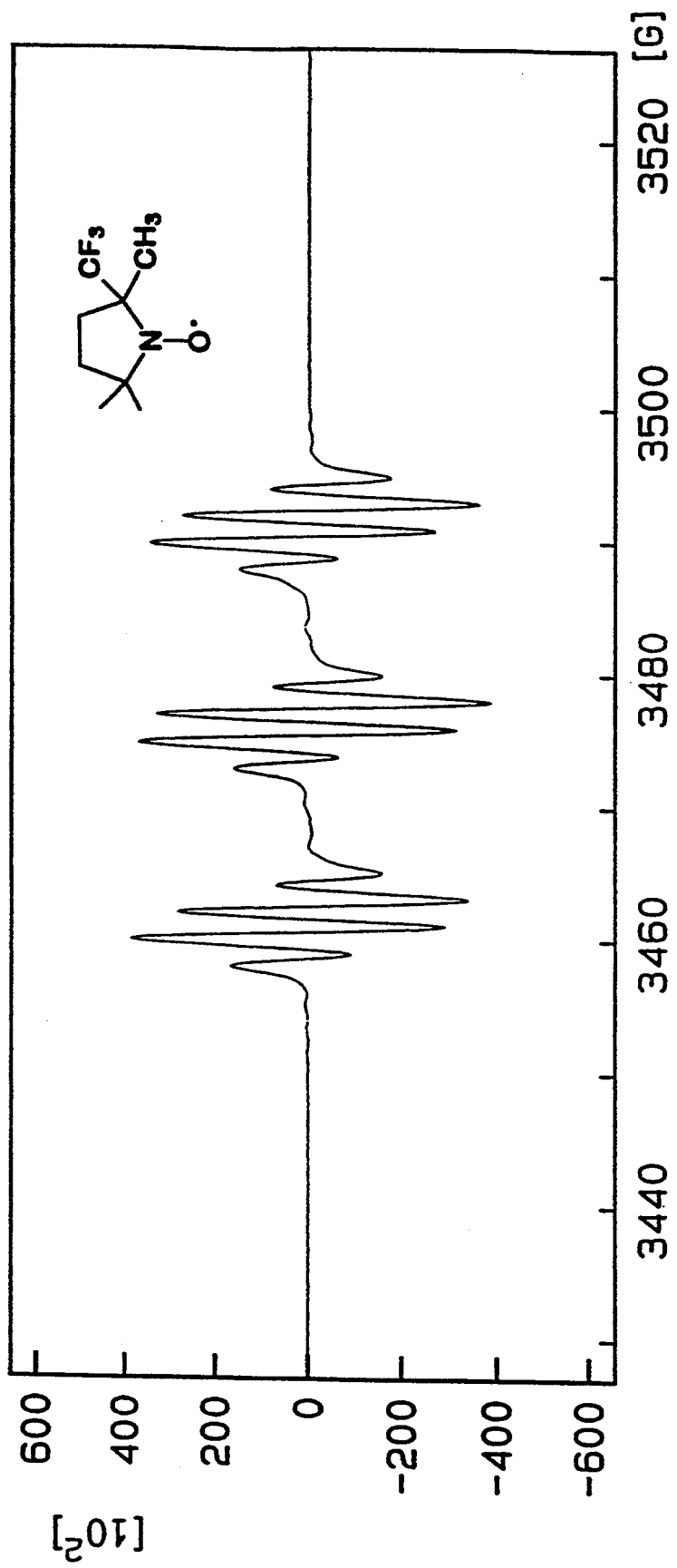
FIG. 15 is EPR data on 2-CF$_3$-DMPO/methyl adduct.
Figure 16:
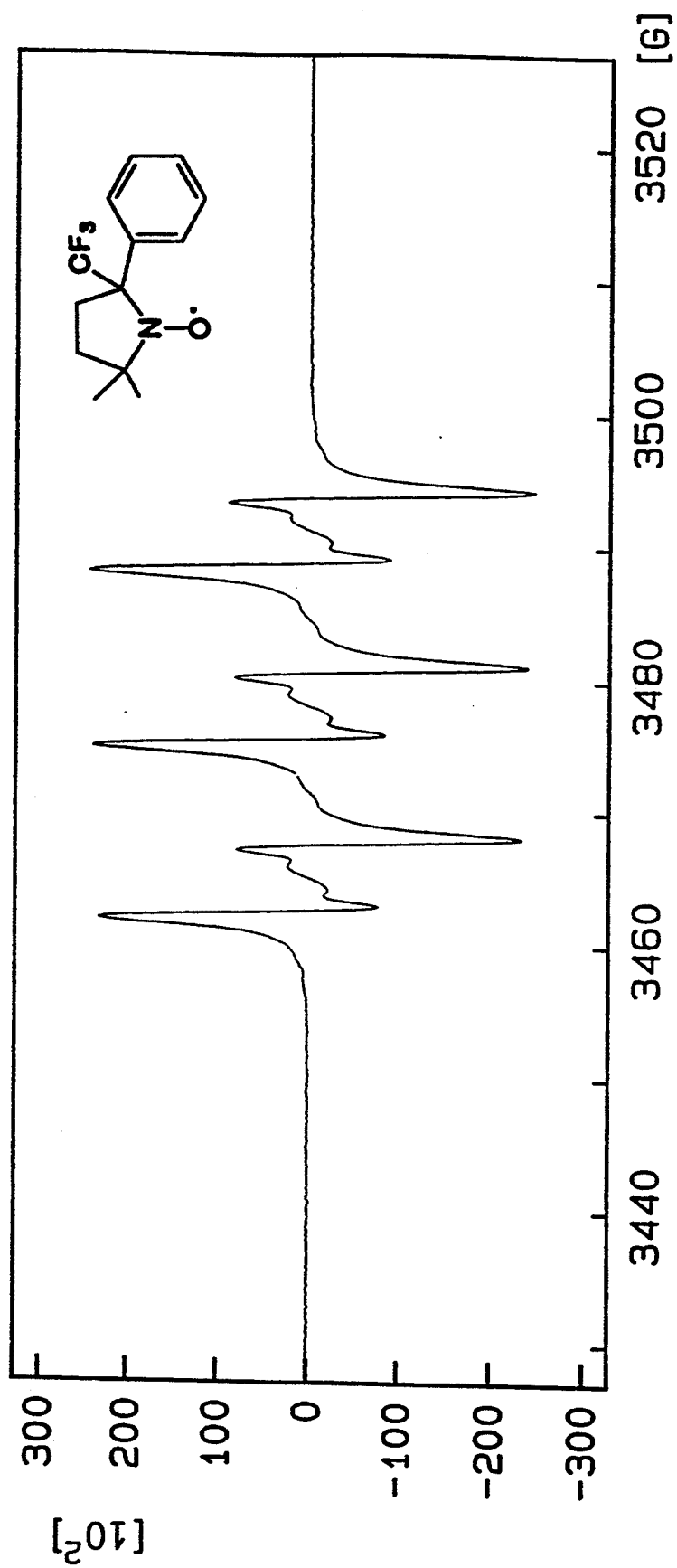
FIG. 16 is EPR data on 2-CF$_3$-DMPO/phenyl adduct.
Figure 17:
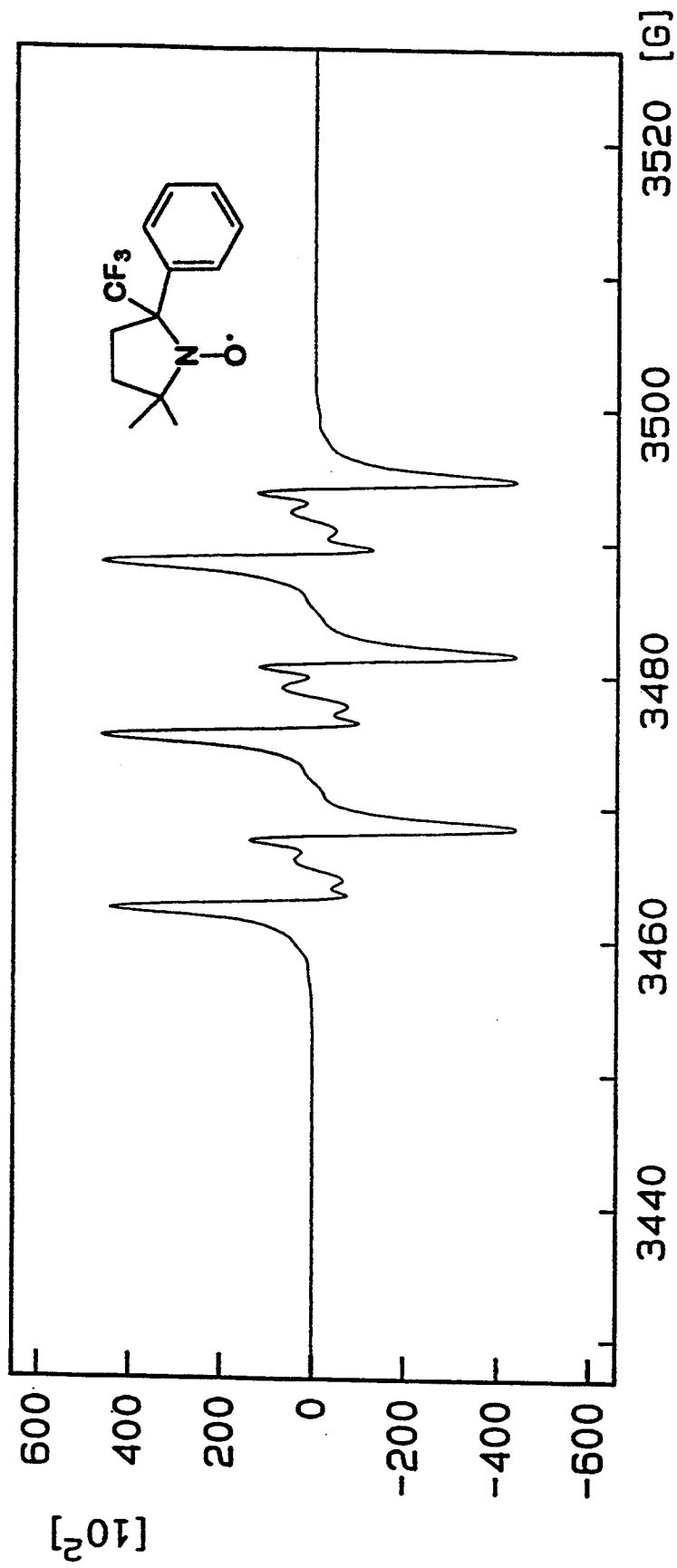
FIG. 17 is EPR data on 2-CF$_3$-DMPO/phenyl adduct.

| | EPR SETTINGS FOR FIGS. 14–17 | | | |
|---|---|---|---|---|
| | FIG. 14 | FIG. 15 | FIG. 16 | FIG. 17 |
| Receiver | | | | |
| Receiver Gain | 2.00e + 05 | 1.60e + 04 | 2.00e + 04 | 2.00e + 04 |
| Phase (deg) | 0 | 0 | 0 | 0 |
| Harmonic | 1 | 1 | 1 | 1 |
| Mod Freq (kHz) | 100.0000 | 100.0000 | 100.0000 | 100.0000 |
| Mod Amplitude (G) | 0.101 | 1.011 | 1.011 | 1.011 |
| Signal Channel | | | | |
| Conversion (ms) | 81.92 | 81.92 | 81.92 | 81.92 |
| Time Const (ms) | 40.96 | 40.96 | 40.96 | 163.84 |
| Sweep Time (s) | 83.886 | 83.886 | 83.886 | 83.886 |
| Scale | 16 | 17 | 16 | 17 |
| Field | | | | |
| Center Field (G) | 3477.00 | 3477.00 | 3477.00 | 3477.00 |
| Sweep Width (G) | 100.00 | 100.00 | 100.00 | 100.00 |
| Resolution (points) | 1024 | 1024 | 1024 | 1024 |
| Comment: | 2-CF$_3$DMPO (.02M) & 1.25% v.Bu$_3$SnD C$_6$H$_6$.UV5s | 2-CF$_3$DMPO (.02M) & 1% H$_2$O$_2$ & 10% v. DMSO.H$_2$O.UV 5s + 5s + 5s | 2-CF$_3$—DMPO (.02M) + (PhCOO)$_2$ C$_6$H$_6$.sample2 | 2-CF$_3$—DMPO (.02M) & 0.5% v. PhCO$_2$OBu-t C$_6$H$_6$.UV4s + 5s + 10s.Ph radical |

TABLE 2E

Figure 18:
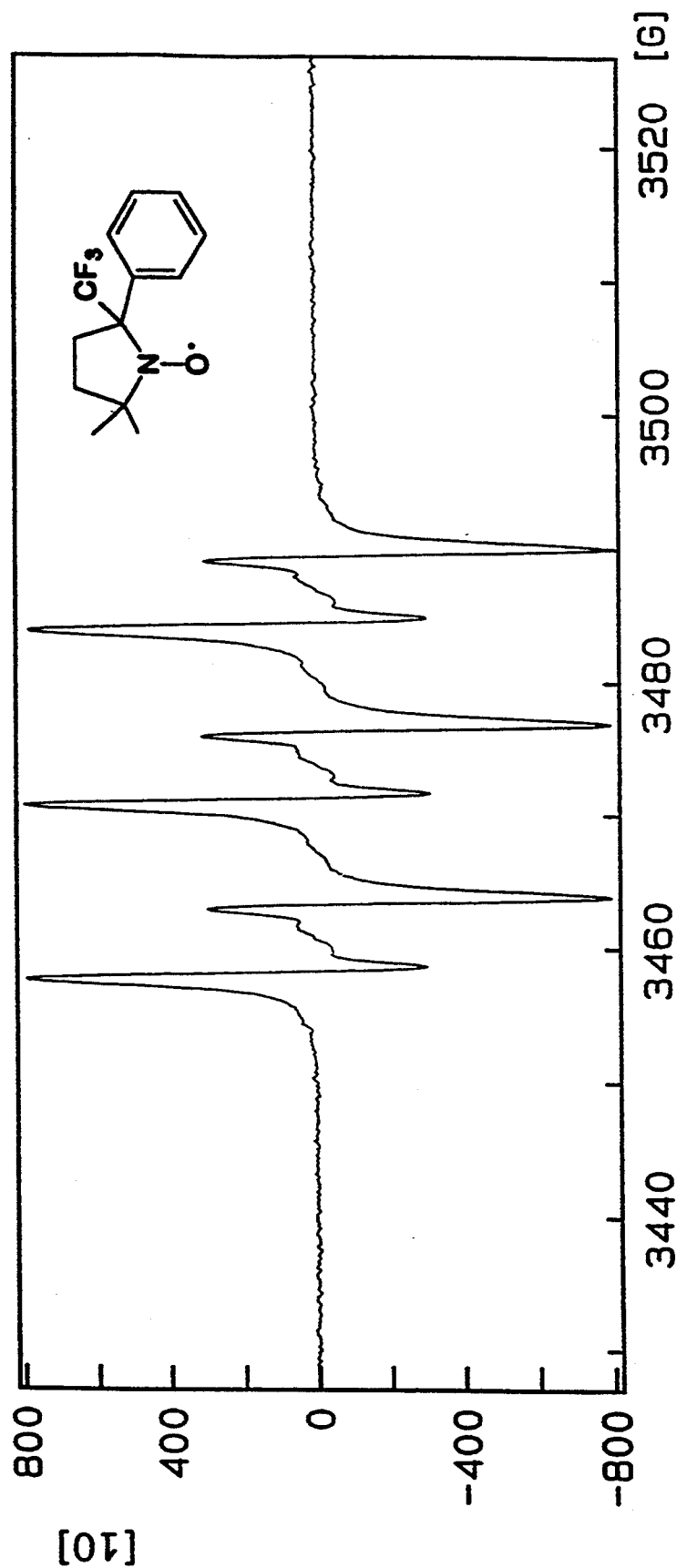
FIG. 18 is EPR data on 2-CF$_3$-DMPO/phenyl adduct from Grignard reaction.
Figure 19:
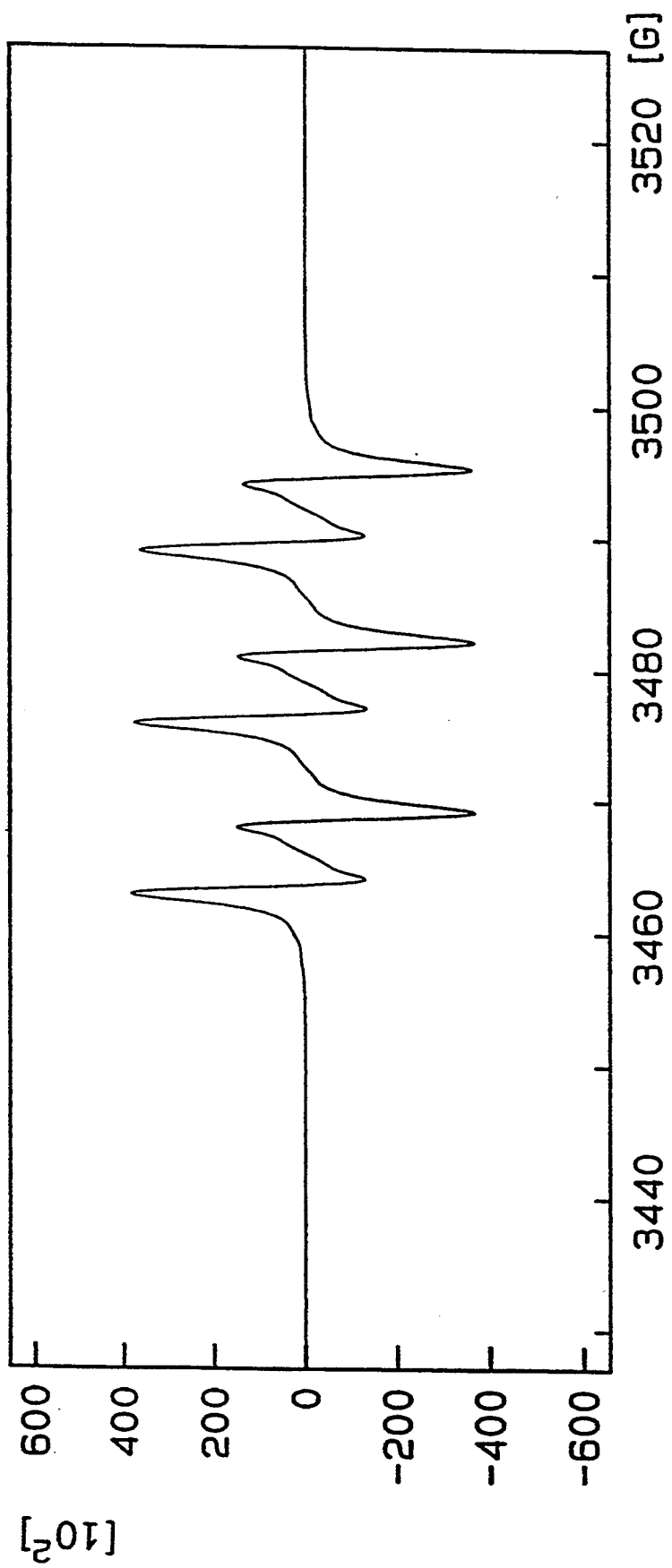
FIG. 19 is EPR data on 2-CF$_3$-DMPO/phenyl adduct in C$_6$H$_6$ purified.
Figure 20:
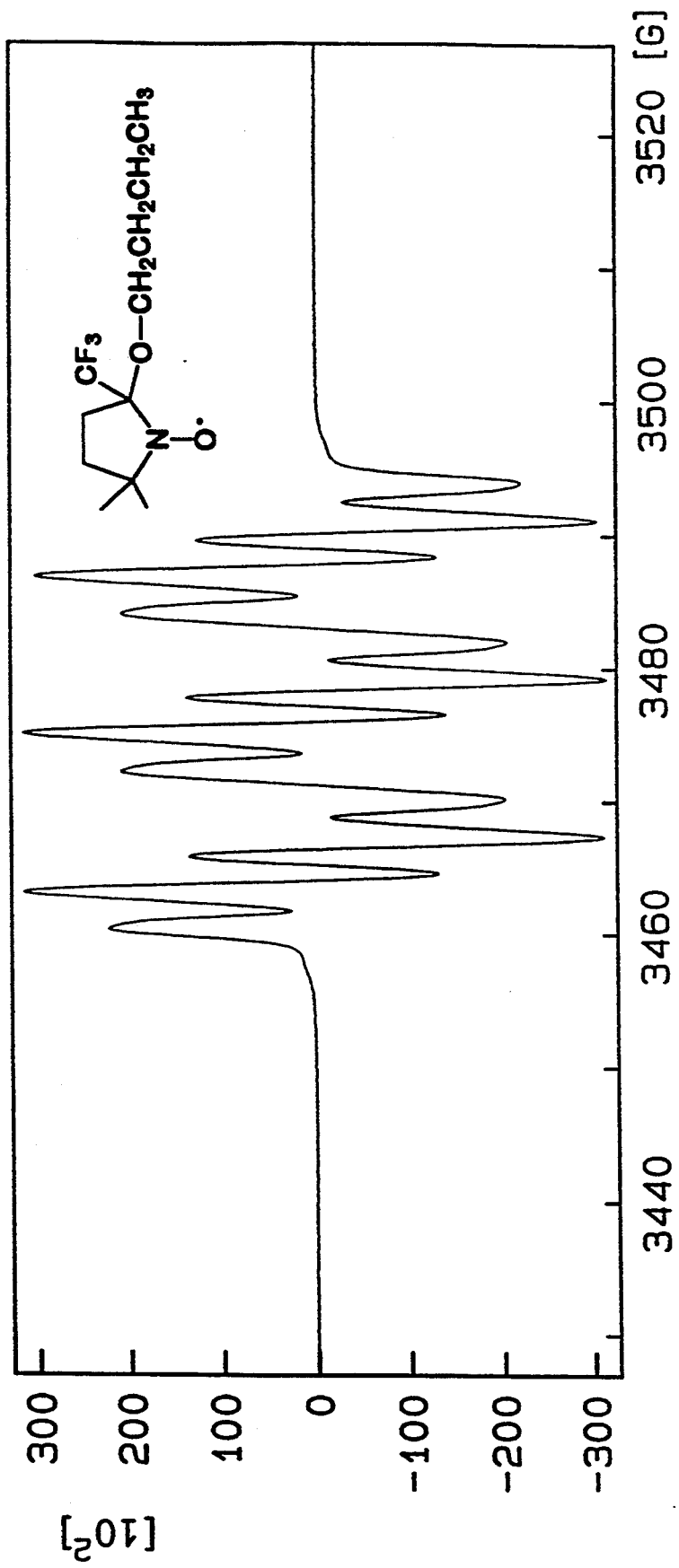
FIG. 20 is EPR data on 2-CF$_3$-DMPO/n-butyloxy adduct.

| | EPR SETTINGS FOR FIGS. 18–20 | | |
|---|---|---|---|
| | FIG. 18 | FIG. 19 | FIG. 20 |
| Receiver | | | |
| Receiver Gain | 1.00e + 03 | 1.00e + 03 | 1.00e + 04 |
| Phase (deg) | 0 | 0 | 0 |
| Harmonic | 1 | 1 | 1 |
| Mod Freq (kHz) | 100.0000 | 100.0000 | 100.0000 |
| Mod Amplitude (G) | 1.011 | 1.011 | 1.011 |
| Signal Channel | | | |
| Conversion (ms) | 81.92 | 81.92 | 81.92 |
| Time Const (ms) | 40.96 | 163.84 | 40.96 |
| Sweep Time (s) | 83.886 | 83.886 | 83.886 |
| Scale | 14 | 17 | 16 |
| Field | | | |
| Center Field (G) | 3477.00 | 3477.00 | 3477.00 |
| Sweep Width (G) | 100.00 | 100.00 | 100.00 |
| Resolution (points) | 1024 | 1024 | 1024 |
| Comment: | 2-CF$_3$—DMPO— Ph Radical C$_6$H$_6$. from Grignard Reaction. | 2-CF$_3$-2-Phenyl- DMPOxyl Radical in C$_6$H$_6$.pure | CF$_3$DMPO (.02M) + 1 μL n-BuONO C$_6$H$_6$. UV 2s. 2-CF$_3$— DMPO—OBu-n. |

EXAMPLE 4

2-CF$_3$-DMPO will be administered to an animal either orally or intraperitoneally in amounts of about 25–250 mg/kg.

An effective amount of 2-CF$_3$-DMPO will be administered to trap the anticipated concentration of free radicals generated in the particular disease state of the patient.

EXAMPLE 5

A method for in vivo spin trapping is conducted according to Lai, et al., *Arch. Biochem. Biophys.* 244:156–160 (1986) which is hereby incorporated by reference. 2-CF$_3$-DMPO or derivatives thereof are tested for effectiveness in treating various diseases.

EXAMPLE 6

Use of 2-CF$_3$-DMPO For Diagnostic Purposes

The spin trap is labeled with a radioactive tag and administered to an animal suspected to have free-radical induced disease. The tag is monitored to determine the site of free radical generation in the animal. The spin adduct could be monitored in blood or urine samples. (A spin adduct is the product of the radical plus the spin trap).

TABLE 3

Hyperfine Splitting Constants (HFSCs) for 2-CF$_3$—DMPO Adducts

| Radical of | Resource | Solvent | $a_N$ (G) | $a_F$ (G) | $a^{\gamma}_H$ (G) |
|---|---|---|---|---|---|
| O$_2^-$ | 30% H$_2$O$_2$ + hv | 30% H$_2$O$_2$ | 13.14 | 2.80(3F) | 0.83(2H) |
|  |  |  |  | t$_{\frac{1}{2}}$ = 12.8 seconds |  |
| SO$_4^-$ | Na$_2$S$_2$O$_8$ | H$_2$O | 12.97 | 3.21(3F) | persistent |
| SO$_4^-$ | simulation | — | 12.97 | 3.21(3F) | 0.83 |
| OH | 1% H$_2$O$_2$ + hv | H$_2$O | 13.98 | 2.70(3F) | — |
| n-butyloxy | n-butylnitrite + hv | Benzene | 11.88 | 2.74(3F) | 0.79(2H) |
| n-butyloxy | simulation | — | 11.88 | 2.74(3F) | 1.05(2H) |
|  |  |  |  | t$_{\frac{1}{2}}$ = 5.8 hours |  |
| i-butyloxy | i-butylnitrite + hv | Benzene | 11.83 | 2.69(3F) | 0.79(2H) |
| i-butyloxy | simulation | — | 11.83 | 2.69(3F) | 1.05(2H) |
| i-amyloxy | i-amylnitrite + hv | Benzene | 11.83 | 2.74(3F) | 0.75(2H) |
| i-amyloxy | simulation | — | 11.83 | 2.69(3F) | 1.05(2H) |
| HOCH$_2$ | 1% H$_2$O$_2$ + methanol + hv | H$_2$O | 14.42 | 2.33(3F) | — |
| HO—$\dot{\text{C}}$(H)—CH$_3$ | 1% H$_2$O$_2$ + ethanol + hv | H$_2$O | 14.47 | 2.87(3F) | — |
| HO—$\dot{\text{C}}$(H)—CH$_2$CH$_3$ | 1% H$_2$O$_2$ + n-propanol + hv | H$_2$O | 14.52 | 2.74(3F) | — |
| (CH$_3$)$_2$COH | 1% H$_2$O$_2$ + i-propanol + hv | H$_2$O | 14.32 | 2.93(3F) | — |
| tetrahydro-furyl | 1% H$_2$O$_2$ + tetrahydrofuran + hv | H$_2$O | 14.37 | 2.64(3F) | — |
| HOCH$_2$CHOH | 1% H$_2$O$_2$ + (HOCH$_2$)$_2$ | H$_2$O | 14.37 | 2.64(3F) | — |
| H | 2.5% Bu$_3$SnH + hv | Benzene | 13.20 | 1.14(3F) | 15.40(1 β-H) |
| Bu$_3$Sn (?) | >7.5% Bu$_3$SnH + hv | Benzene | 27.83 | — |  |
| Bu$_3$Sn (?) | >1.25% Bu$_3$SnD + hv | Benzene | 27.83 | — |  |
| CH$_3$ | 1% H$_2$O$_2$ + DMSO + hv | H$_2$O | 14.90 | 2.05(3F) | — |
| Ethyl | Grignard reaction | H$_2$O | 14.66 | 2.51(3F) | — |
| Ethyl | Grignard reaction | Benzene | 12.93 | 2.64(3F) | — |
| C$_6$H$_5$ | (PhCOO)$_2$ + hv | Benzene | 13.07 | 4.88(a$_F^1$ + a$_F^2$ + a$_F^3$) |  |
| C$_6$H$_5$ | PhCOOOC(CH$_3$) + hv | Benzene | 13.05 | 4.88(a$_F^1$ + a$_F^2$ + a$_F^3$) |  |
| C$_6$H$_5$ | PhMgBr adduct, H$_2$O, then oxidized purified, pure | Benzene | 13.05 | 4.97(a$_F^1$ + a$_F^2$ + a$_F^3$) |  |
|  |  | H$_2$O | 14.54 | 4.66(a$_F^1$ + a$_F^2$ + a$_F^3$) |  |
| CO$_2^-$ | 1% H$_2$O$_2$ + HCOONa | H$_2$O | 14.57 | 5.23(a$_F^1$ + a$_F^2$ + a$_F^3$) |  |
| CO$_2^-$ | 2% H$_2$O$_2$ + HCOONa | H$_2$O | 14.55 | 5.27(a$_F^1$ + a$_F^2$ + a$_F^3$) |  |

Legend: hv = ultraviolet radiation for seconds, mercury arc; t$_{\frac{1}{2}}$ = the time required for 50% of the adduct to decay; G - gauss; (?) indicates precise identity of radical formed from indicated reaction is uncertain; D = Heavy hydrogen of $^2$H; DMSO = dimethylsulfoxide; Ph = phenyl

We claim:

1. A chemical composition of the formula:

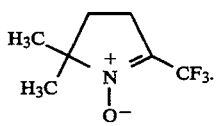

2. A chemical composition of the formula

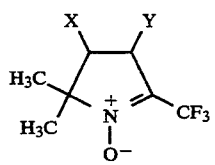

where X is alkyl (CH$_2$)$_n$H where n=(1, 2 . . . 18); aryl; (CH$_2$)$_n$ COOR where n=(0, 1, 2 . . . 18) and R=H, CH$_3$, CH$_3$—CH$_2$, or Group IA metal ions; (CH$_2$)$_n$ P(O) (OR)$_2$ where n=(0, 1, 2, . . . 18), R=H, CH$_3$, CH$_3$—CH$_2$, or Group IA metal ions, and Y is alkyl (CH$_2$)$_n$H where n=(1, 2 . . . 18) aryl; (CH$_2$)$_n$ COOR where n=(0, 1, 2 . . . 18) and R=H, CH$_3$, CH$_3$—CH$_2$, or Group IA metal ions; (CH$_2$)$_n$ P(O) (OR)$_2$ where n=( 0, 1, 2, . . . 18 ) , R=H, CH$_3$ , CH$_3$—CH$_2$, or Group IA metal ions, and wherein X can be the same or different from Y in a given molecule.

3. A method for synthesizing 5,5-dimethyl-2-trifluoromethyl-1-pyrroline N-oxide, comprising the steps of:

a) reducing ethyl 4,4,4-trifluoroacetoacetate to form ethyl 3-hydroxy-4,4,4-trifluorobutyrate;

b) reducing said ethyl 3-hydroxy-4,4,4-trifluorobutyrate to form 2,4-dihydroxy-1,1,1-trifluorobutane;

c) selectively monotosylating said 2,4-dihydroxy-1,1,1-trifluorobutane to form 2-hydroxy-4-tosyloxy-1,1,1-trifluorobutane;

d) oxidizing said 2-hydroxy-4-tosyloxy-1,1,1-trifluorobutane with

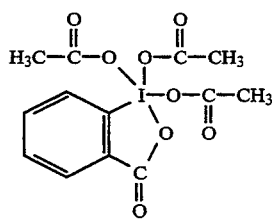

to form 4-tosyloxy-1,1,1-trifluoro-2-butanone;

e) treating said 4-tosyloxy-1,1,1-trifluoro-2-butanone with $(CH_3)_2 C(Na)NO_2$ in ethanol to generate 5-methyl-5-nitro-1,1,1-trifluoro-2-hexanone; and f) reducing said 5-methyl-5-nitro-1,1,1-trifluoro2-hexanone to form said 5,5-dimethyl-2-trifluoro methyl-1-pyrroline N-oxide.

TABLE 2A

| EPR SETTINGS FOR FIGS. 2-5 | | | | |
|---|---|---|---|---|
| | FIG. 2 | FIG. 3 | FIG. 4 | FIG. 5 |
| Receiver | | | | |
| Receiver Gain | 1.00e + 05 | 2.50e + 04 | 1.00e + 04 | 1.00e + 04 |
| Phase (deg) | 0 | 0 | 0 | 0 |
| Harmonic | 1 | 1 | 1 | 1 |
| Mod Freq (kHz) | 100.0000 | 100.0000 | 100.0000 | 100.0000 |
| Mod Amplitude (G) | 0.254 | 1.011 | 1.011 | 1.011 |
| Signal Channel | | | | |
| Conversion (ms) | 40.96 | 81.92 | 81.92 | 81.92 |
| Time Const (ms) | 81.92 | 40.96 | 40.96 | 40.96 |
| Sweep Time (s) | 41.943 | 83.886 | 83.886 | 83.886 |
| Scale | 16 | 16 | 16 | 16 |
| Field | | | | |
| Center Field (G) | 3477.00 | 3477.00 | 3477.00 | 3477.00 |
| Sweep Width (G) | 100.00 | 100.00 | 100.00 | 100.00 |
| Resolution (points) | 1024 | 1024 | 1024 | 1024 |
| Comment: | 2-$CF_3$ DMPO (1% v.) in 30% $H_2O_2$.UV3s | 2-$CF_3$—DMPO (.02M) & 1% $H_2O_2.H_2O$.UV 3s + 3s.$CF_3$ DMPO—OH Radical | $CF_3$DMPO (.02M) + 1 μL iso-BuONO $C_6H_6$.UV2s.2-$CF_3$—DMPO—OBu-iso. | $CF_3$DMPO (.02M) + 1 μL iso-Amyl—ONO $C_6H_6$.UV2s. iso-AmylO-2-$CF_3$DMPO. |

TABLE 2B

| EPR SETTINGS FOR FIGS. 6-9 | | | | |
|---|---|---|---|---|
| | FIG. 6 | FIG. 7 | FIG. 8 | FIG. 9 |
| Receiver | | | | |
| Receiver Gain | 1.60e + 04 | 2.50e + 04 | 2.00e + 04 | 2.00e + 04 |
| Phase (deg) | 0 | 0 | 0 | 0 |
| Harmonic | 1 | 1 | 1 | 1 |
| Mod Freq (kHz) | 100.0000 | 100.0000 | 100.0000 | 100.0000 |
| Mod Amplitude (G) | 1.011 | 1.011 | 1.011 | 1.011 |
| Signal Channel | | | | |
| Conversion (ms) | 81.92 | 81.92 | 81.92 | 81.92 |
| Time Const (ms) | 40.96 | 40.96 | 40.96 | 40.96 |
| Sweep Time (s) | 83.886 | 83.886 | 83.886 | 83.886 |
| Scale | 16 | 16 | 15 | 15 |
| Field | | | | |
| Center Field (G) | 3477.00 | 3477.00 | 3477.00 | 3477.00 |
| Sweep Width (G) | 100.00 | 100.00 | 100.00 | 100.00 |
| Resolution (points) | 1024 | 1024 | 1024 | 1024 |
| Comment: | 2-$CF_3$—DMPO (.02M) & 1% $H_2O_2$ & 10% v. MeOH.$H_2O$.UV5s. $CF_3$DMPO—$CH_2$OH | 2-$CF_3$—DMPO (.02M) & 1% $H_2O_2$ & 10% v. EtOH.$H_2O$.UV3s. 2-$CF_3$DMPO—CH (OH) Me. | 2-$CF_3$DMPO (.02M) & 1% $H_2O_2$ & 10% v. $EtCH_2OH.H_2O$. UV5s | 2-$CF_3$DMPO (.02M) & 1% $H_2O_2$ & 10% v. iso-$EtCH_2OH$. $H_2O$.UV5s + 10s + 10s + 10s |

TABLE 2C

| EPR SETTINGS FOR FIGS. 10-13 | | | | |
|---|---|---|---|---|
| | FIG. 10 | FIG. 11 | FIG. 12 | FIG. 13 |
| Receiver | | | | |
| Receiver Gain | 1.00e + 04 | 5.00e + 04 | 1.00e + 05 | 1.00e + 05 |
| Phase (deg) | 0 | 0 | 0 | 0 |
| Harmonic | 1 | 1 | 1 | 1 |
| Mod Freq (kHz) | 100.0000 | 100.0000 | 100.0000 | 100.0000 |
| Mod Amplitude (G) | 1.011 | 1.011 | 0.320 | 0.113 |
| Signal Channel | | | | |
| Conversion (ms) | 81.92 | 81.92 | 81.92 | 81.92 |
| Time Const (ms) | 40.96 | 40.96 | 40.96 | 40.96 |
| Sweep Time (s) | 83.886 | 83.886 | 83.886 | 83.886 |
| Scale | 17 | 17 | 15 | 16 |
| Field | | | | |
| Center Field (G) | 3477.00 | 3477.00 | 3477.00 | 3477.00 |
| Sweep Width (G) | 100.00 | 100.00 | 100.00 | 100.00 |
| Resolution (points) | 1024 | 1024 | 1024 | 1024 |
| Comment: | 2-$CF_3$DMPO (.02M) & 1% $H_2O_2$ & 10% v. THF.$H_2O$.UV5s + | 2-$CF_3$DMPO (.02M) & 1% $H_2O_2$ & 10% v. $HOCH_2CH_2OH$. | 2-$CF_3$DMPO (.02M) & 2.5% v.$Bu_3SnH$ $C_6H_6$.UV5s + 5s | 2-$CF_3$DMPO (.02M) & 7.5% v.$Bu_3SnH$ $C_6H_6$.UV10s again |

TABLE 2C-continued

EPR SETTINGS FOR FIGS. 10-13

| FIG. 10 | FIG. 11 | FIG. 12 | FIG. 13 |
|---|---|---|---|
| 20s.$CF_3$—DMPO—THF Radical | $H_2O$.UV5s + 23s + 20s | | |

TABLE 2D

EPR SETTINGS FOR FIGS. 14-17

| | FIG. 14 | FIG. 15 | FIG. 16 | FIG. 17 |
|---|---|---|---|---|
| Receiver | | | | |
| Receiver Gain | 2.00e + 05 | 1.60e + 04 | 2.00e + 04 | 2.00e + 04 |
| Phase (deg) | 0 | 0 | 0 | 0 |
| Harmonic | 1 | 1 | 1 | 1 |
| Mod Freq (kHz) | 100.0000 | 100.0000 | 100.0000 | 100.0000 |
| Mod Amplitude (G) | 0.101 | 1.011 | 1.011 | 1.011 |
| Signal Channel | | | | |
| Conversion (ms) | 81.92 | 81.92 | 81.92 | 81.92 |
| Time Const (ms) | 40.96 | 40.96 | 40.96 | 163.84 |
| Sweep Time (s) | 83.886 | 83.886 | 83.886 | 83.886 |
| Scale | 16 | 17 | 16 | 17 |
| Field | | | | |
| Center Field (G) | 3477.00 | 3477.00 | 3477.00 | 3477.00 |
| Sweep Width (G) | 100.00 | 100.00 | 100.00 | 100.00 |
| Resolution (points) | 1024 | 1024 | 1024 | 1024 |
| Comment: | 2-$CF_3$DMPO (.02M) & 1.25% v.$Bu_3$SnD $C_6H_6$.UV5s | 2-$CF_3$DMPO (.02M) & 1% $H_2O_2$ & 10% v. DMSO.$H_2O$.UV 5s + 5s + 5s | 2-$CF_3$—DMPO (.02M) + (PhCOO)$_2$ $C_6H_6$.sample2 | 2-$CF_3$—DMPO (.02M) & 0.5% v. $PhCO_2OBu$-t $C_6H_6$.UV4s + 5s + 10s.Ph radical |

TABLE 2E

EPR SETTINGS FOR FIGS. 18-20

| | FIG. 18 | FIG. 19 | FIG. 20 |
|---|---|---|---|
| Receiver | | | |
| Receiver Gain | 1.00e + 03 | 1.00e + 03 | 1.00e + 04 |
| Phase (deg) | 0 | 0 | 0 |
| Harmonic | 1 | 1 | 1 |
| Mod Freq (kHz) | 100.0000 | 100.0000 | 100.0000 |
| Mod Amplitude (G) | 1.011 | 1.011 | 1.011 |
| Signal Channel | | | |
| Conversion (ms) | 81.92 | 81.92 | 81.92 |
| Time Const (ms) | 40.96 | 163.84 | 40.96 |
| Sweep Time (s) | 83.886 | 83.886 | 83.886 |
| Scale | 14 | 17 | 16 |
| Field | | | |
| Center Field (G) | 3477.00 | 3477.00 | 3477.00 |
| Sweep Width (G) | 100.00 | 100.00 | 100.00 |
| Resolution (points) | 1024 | 1024 | 1024 |
| Comment: | 2-$CF_3$—DMPO—Ph Radical $C_6H_6$. from Grignard Reaction. | 2-$CF_3$-2-Phenyl-DMPOxyl Radical in $C_6H_6$.pure | $CF_3$DMPO (.02M) + 1 μL n-BuONO $C_6H_6$. UV 2s. 2-$CF_3$—DMPO—OBu-n. |

* * * * *

UNITED STATES PATENT AND TRADEMARK OFFICE
CERTIFICATE OF CORRECTION

PATENT NO.   : 5,405,967
DATED        : Apr. 11, 1995
INVENTOR(S)  : Janzen et al.

It is certified that error appears in the above-indentified patent and that said Letters Patent is hereby corrected as shown below:

Column 1, line 5, after the title, insert:

--                 GOVERNMENT RIGHTS

The invention described herein was made with government support under Grant No. RRO-5517 awarded by The National Institutes of Health. The government has certain rights in the ivention.--

Signed and Sealed this

Nineteenth Day of September, 1995

*Attest:*

BRUCE LEHMAN

*Attesting Officer*      *Commissioner of Patents and Trademarks*